United States Patent
Kaddurah-Daouk et al.

(10) Patent No.: US 6,720,188 B2
(45) Date of Patent: Apr. 13, 2004

(54) METHODS AND KITS FOR THE DETECTION OF ARGININE COMPOUNDS

(75) Inventors: Rima Kaddurah-Daouk, Belmont, MA (US); Thomas W. Bell, 4775 Summit Ridge Pl., Apt. #1097, Reno, NV (US) 89803; Alisher B. Khasanov, Carlsbad, CA (US)

(73) Assignees: FAL Diagnostics, Portland, OR (US); Thomas W. Bell, Reno, NV (US)

(*) Notice: Subject to any disclaimer, the term of this patent is extended or adjusted under 35 U.S.C. 154(b) by 0 days.

(21) Appl. No.: 09/900,495

(22) Filed: Jul. 5, 2001

(65) Prior Publication Data

US 2002/0081626 A1 Jun. 27, 2002

Related U.S. Application Data

(60) Provisional application No. 60/216,180, filed on Jul. 6, 2000.

(51) Int. Cl.$^7$ ............................................... G01N 33/00
(52) U.S. Cl. ........................ 436/86; 436/164; 436/172; 435/69.6; 435/69.7
(58) Field of Search ............................. 435/69.6, 69.7; 436/86, 164, 172

(56) References Cited

U.S. PATENT DOCUMENTS

| | | | |
|---|---|---|---|
| 5,030,728 A | 7/1991 | Bell | 546/27 |
| 5,128,466 A | 7/1992 | Bell | 540/452 |
| 5,283,333 A | 2/1994 | Bell | 546/27 |

FOREIGN PATENT DOCUMENTS

| | | |
|---|---|---|
| JP | 08 338826 | 12/1996 |
| WO | WO 00/46395 A1 | 8/2000 |
| WO | WO 01/55719 A2 | 8/2001 |

OTHER PUBLICATIONS

Julian et al. "Molecular recognition of arginine in small peptides by supramolecular complexation with dibenzo–30–crown–10 ether" International Journal of Mass Spectrometry (2002), 220(1), 87–96.*

Magun et al. "New fluorescent method with phenanthrene-quinone for the histochemical demonstration of arginine residues in tissues", Journal of Histochemistry and Cytochemistry (1969), 17(12), 821–7.*

Eliseev et al. :Use of Molecular Recognition to Drive Chemical Evolution . . . , J. Am.Chem. Soc., 1997, v. 119, pp. 1147–1148.*

Beckles, D.L. et al. "Complexation of creatinine by synthetic receptors," *Tetrahedron* (1995) 51:363–376.

Bell, T.W. et al. "Hexagonal lattice hosts for urea. A new series of designed heterocyclic receptors," *J. Am. Chem. Soc.* (1988) 110:3673–3674.

Bell, T.W. et al. "Torand synthesis by trimerization. New receptors for guanidinium," *Angew. Chem. Int. Ed. Engl.*, (1990) 29:923–925.

Bell, T.W. et al. "Detection of creatinine by a designed receptor," *Science* (1995) 269(5224):671–4.

Bell, T.W. et al. "A hydrogen–bonding receptor that binds urea with high affinity," *Angew. Chem. Int. Ed. Engl.* (1997) 36: 1536–1538.

Bell, T.W. et al. "Hydrogen bonding chemosensors for metabolites and nucleotides," In *Chemosensors of Ion and Molecule Recognition*, J.P. Desvergne, A. Czarnik, Eds., Kluwer:Dordrecht, The Netherlands, 1997, pp. 121–132.

Bell, T.W. et al. "A small–molecule guanidinium receptor: The arginine cork," *Angew. Chem., Int. Ed. Engl.*, 1999, 38, 2543–2547.

Bode–Böger, S. M. et al., "Elevated L–arginine/dimethylarginine ration contributes to enhanced systematic NO production by dietary L–arginine in hypercholesterolemic rabbits," *Biochem. Biophys. Res. Commun.* (1996) 219:598–603.

Böger, R. H. et al. "Dietary L–Arginine reduces the progression of Atherosclerosis in cholesterol–fed rabbits; Comparison with lovastatin," *Circulation* (1997) 96:1282–1290.

Böger, R. H. et.al. "Asymmetric dimethylarginine (ADMA): A novel risk factor for endothelial dysfunction. Its role in hypercholesterolemia," *Circulation* (1998) 98:1842–1847.

Chulananda, D.A. et al. "Nitric oxide synthase inhibitors and hypertension in children and adolescents," *J. Hypertension* (1997) 15:901–909.

Cram, D.J. "Preorganization. From solvents to spherands," *Angew. Chem. Int. Ed. Engl.* (1986) 25:1039–1134.

Das, I. et al. "Elevated endogenous nitric oxide synthase inhibitor in schizophrenic plasma may reflect abnormalities in brain nitric oxide production," *Neurosci Lett.* (1996) 215:209–211.

Fändriks, L. et al. "Water extract of helicobacter pylori inhibits duodenal mucosal alkaline secretion in anesthetized rats," *Gastroenterology* (1997) 113:1570–1575.

Herlitz et al. "The Arginine–Nitric Oxide pathway in thrombotic microangiopathy," *Scand. J. Urol. Nephrol.* (1997) 31:477–479.

Ito, A. "Novel mechanism for endothelial dysfunction. Dysregulation of dimethylarginine dimethylaminohydrolase," *Cir.* (1999) 99(34):3092–5.

(List continued on next page.)

*Primary Examiner*—Jill Warden
*Assistant Examiner*—Yelena Gakh
(74) *Attorney, Agent, or Firm*—Lahive & Cockfield, LLP; Elizabeth A. Hanley, Esq.; Cynthia M. Soroos, Esq.

(57) ABSTRACT

Methods and kits for determine arginine compounds are discussed. The methods and kits of the invention can be used for the diagnosis of arginine compound associated disorders.

35 Claims, No Drawings

OTHER PUBLICATIONS

Macallister, R. J. et al. "Effects of guanidino a nd uremic compounds on nitric oxide pathways," *Kidney Int.* (1994) 45:737–742.

Macallister, R. J. et al. "Concentration of dimethyl–L–arginine in the plasma of patients with end–stage renal failure," *Nephrol Dial. Transplant.* (1996) 11:2449–2452.

Macallister, R. J et.al. "Regulation of nitric oxide synthesis by dimethylarginine dimethylaminohydrolase," *Br. J. Pharmacol.* (1996) 119:1533–1540.

Masuda, H. et al. "Accelerated intimal hyperplasia and increased endogenous inhibitors for NO synthesis in rabbits with alloxan–induced hyperglycaemia," *Br. J. Pharmacol.* (1999) 126:211–218.

Miyazaki, H. et al. "Endogenous nitrix oxide synthase inhibitor. A novel marker of atherosclerosis," *Circulation* (1999) 99:1141–1146.

Petros, A. et al. "Effects of a nitric oxide synthase inhibitor in humans with septic shock," *Cardiovascular Res.* (1994) 28:34–39.

Tag, K. et al. "Arxula adeninivorans LS3 as a suitable biosensor for measurements of biodegradable substances in salt water," *J. Chem. Tech. Biotech.* (1998) 73(4):385–88.

Vallance et.al. "Accumulation of an endogenous inhibitor of nitric oxide synthesis in chronic renal failure," *Lancet* (1992) 339:572–575.

\* cited by examiner

METHODS AND KITS FOR THE DETECTION OF ARGININE COMPOUNDS

RELATED APPLICATIONS

This application claims priority to copending U.S. Provisional Patent Application Ser. No. 60/216,180, entitled "Methods and Kits for the Detection of Arginine Compounds" filed on Jul. 6, 2000.

BACKGROUND OF INVENTION

L-arginine is a substrate for nitric oxide synthases (NO synthases) and is a precursor of nitric oxide (NO), a major cell signaling molecule implicated in the regulation of many cellular pathways. The L-arginine: NO pathway has been implicated in the regulation of the cardiovascular, nervous and immune systems. Inhibitors of NO have been shown to increase blood pressure in guinea pigs and rabbits (Aisaka et al *Biochem. Biophys. Res. Commun.* (1989) 160:-881–886; Rees et al. *PNAS* (1989) 86:3375–3378), and to induce arteriolar vasoconstriction in humans (Vallance et. al. (1989) *Lancet* 8670:997–1000). A variety of arginine analogs were identified which modulate the L-arginine:NO pathway (for review see Leiper and Vallance, *Cardiovascular Research*, 43, 1999, 542–548). These include $N^G$-monomethyl-L-arginine (L-NMMA), $N^G$-, $N^G$-dimethylarginine (ADMA; asymmetric dimethyl arginine) and $N^{G'}$-, $N^G$-dimethylarginine (SDMA; symmetric dimethylarginine).

SUMMARY OF INVENTION

In one embodiment, the invention pertains to a method for determining arginine compound levels in body samples of a subject. The method includes contacting a body sample with an arginine sensing substance, and analyzing the resulting mixture. Examples of preferred body samples include, body fluids such as blood, saliva, sweat and urine. In an advantageous embodiment, the body sample is obtained non-invasively. In particular preferred embodiment, the arginine compound level is analyzed through a color change, e.g., a change in optical characteristics or fluorescence, of the arginine compound sensing substance and body fluid mixture. Such determination could determine need for therapy administration or other interventions. Examples of arginine, $N^G$-compounds include L-arginine and derivatives of arginine such as methyl arginine, monomethyl-L-arginine (L-NMMA), $N^G$, $N^G$-dimethylarginine (ADMA; asymmetric dimethyl arginine) and $N^{G'}$, $N^G$-dimethylarginine (SDMA; symmetric dimethylarginine).

The invention also pertains to a kit suitable for determining arginine compound levels in a subject. Preferably, the kit includes direction for use. In one embodiment of the kit, the arginine sensing substance is embedded in a solid, permeable substrate. In another embodiment the kit includes a vial for mixing an arginine (or arginine compound) sensing substance with a body sample.

The invention also pertains, at least in part, to arginine compound recognizing substances of the formula (I):

$$G(N)_n(C)_m \quad (I)$$

wherein
G is a guanidinium recognizing moiety;
N is an ammonium recognizing moiety;
C is a carboxylate recognizing moiety; and
n and m are each independently integers from 0 to 10.

DETAILED DESCRIPTION OF THE INVENTION

Arginine (Arg) and asymmetric dimethylarginine (ADMA) are present in human bodily fluids, such as serum and urine, and are derived from the catabolism of proteins containing arginine and methylated arginine residues (Cooke, J. P. *Arterioscler. Thromb. Vasc. Biol.* 2000, 2032–2037). Levels of ADMA is further regulated via metabolic pathways, such as the major one involving the enzyme dimethylarginine dimethylaminohydrolase (DDAH). Bodily production of nitric oxide (NO), the critical modulator of blood flow and blood pressure (Rees, D. D.; et al. *PNAS*, 1989, 86, 3375–3378), occurs through metabolism of arginine by the specific enzyme nitric oxide synthase (NOS). While arginine is utilized for NO synthesis, endogenous ADMA, on the contrary, downregulates NO production by inhibiting NOS. Abnormal concentrations of ADMA can serve as indications of various disorders, such as renal failure, endothelial dysfunction, and vascular diseases in general (Cooke, J. P. *Arterioscler. Thromb. Vasc. Biol.* 2000, 2032–2037). Levels of available arginine are very important for NO synthesis in patients with hypercholesterolemia or atherosclerosis. Thus, detection of arginine and ADMA levels in bodily fluids is useful for diagnosis and treatment of these diseases.

The invention pertains, at least in part, to methods and kits for determining levels of arginine compounds in a body sample. In one embodiment, the invention pertains to a diagnostic kit that can detect levels of arginine compounds in body sample. The invention includes methods for determining the appropriate levels of an arginine compound, to administer to a subject who may be suffering from aberrant arginine compound levels due to an arginine compound related disorder.

In one embodiment, the invention pertains to a method for determining arginine compound levels in a body sample. The method includes contacting a body sample with a arginine sensing substance, and analyzing the resulting mixture. Preferably, the arginine sensing substance is a arginine compound recognizing substance.

The term "body sample" includes body fluids and tissues which may potentially contain arginine compounds. The term "body sample" also includes body fluids. The term "body fluids" includes all fluids obtained from a mammalian body, including, for example, blood, plasma, urine, serum, saliva, sweat, and spinal and brain fluids. In an embodiment, the arginine compound is methyl arginine, L-NMMA, ADMA, SDMA or L-arginine. Furthermore, the body sample may be either processed (e.g., serum, crushed cellular material) or unprocessed.

The term "arginine compound" includes L-arginine and derivatives of arginine such as methyl arginine, $N^G$-monomethyl-L-arginine (L-NMMA), $N^G$, $N^G$-dimethylarginine (ADMA; asymmetric dimethyl arginine) and $N^{G'}$, $N^G$-dimethylarginine (SDMA; symmetric dimethylarginine). Other arginine derivatives which can be identified using the methods and compositions of the invention are also included. Certain arginine compounds are shown in Table 1.

TABLE 1

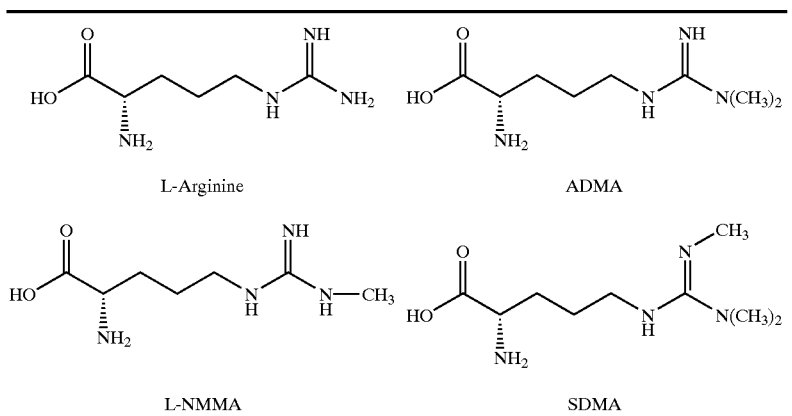

L-Arginine      ADMA

L-NMMA      SDMA

L-NMMA, an arginine compound, has been found to inhibit the cytotoxic effects of activated macrophages and to prevent the release of nitrate and nitrite derived from L-arginine within these cells. After Furchgott's endothelium-derived relaxing factor was identified as nitric oxide (Palmer et. al., Nature (1987) 327:524–526), it was discovered that L-NMMA inhibited the generation of endolethial NO from L-arginine (Palmer et. al., Nature (1988) 333:664–666). Subsequently, L-NMMA became a tool to probe into the functions of the L-arginine:NO pathway.

L-NMMA is found naturally in cells as an arginine analog. Additionally, asymmetric and symmetric dimethylarginines have been identified. These substituted methyl arginine compounds affect arginine handling and modulate NO synthesis and its regulated pathways. Determining levels of arginine and other arginine compounds (e.g., methylated derivatives) in tissues and body fluids has a predictive and diagnostic value in predisposition or progression of NO associated disorders.

The arginine compounds, ADMA and SDMA, are the major circulating forms of methylarginine in humans. The presence of methylated arginine residues was noted within specialized proteins including myelin basic protein, heat shock proteins, nuclear and nucleolar proteins (Lischwe et. al., J. Biol. Chem. (1985) 260:14304–14310; Lischwe et al. Biochemistry (1985) 22:6025–6028) but their function remains unclear. A series of protein-arginine methyl transferase enzymes have been identified (Paik et. al. J Biol. Chem. (1968) 243:2108–2114; Ghosh et. al., J. Biol. Chem. (1988) 263:19024–19033). Some have wide substrate specificity such as histone and non histone nuclear proteins and others are more selective. These enzymes can generate L-NMMA and SDMA methylated arginines or L-NMMA and ADMA methylated arginines. The production of methylarginine residues is highly regulated and results in the regulation of several signalling pathways. Proteolysis of proteins containing methylarginine residues leads to the release of free methylarginine residues into the cytoplasm (Kakimoto et. al., J. Biol. Chem. (1970) 245:5751–5758).

Initially it was assumed that following proteolysis the released methylarginine are released into the plasma and cleared by kidney without further catabolism. However, in 1987 Sasaoka and co-workers demonstrated the existence of a pathway for the catabolism of ADMA to citrulline and dimethyl amine in rats (Ogawa et. al., Arch Biochem Biophys (1987) 252:526–537). Enzymes such as dimethylarginine dimethylaminohydrolase have been identified (Ogawa et. al., J. Biol. Chem. (1989) 264:10205–10209). Hence both the synthesis and metabolism of methylarginines are highly regulated in normal states.

L-NMMA and ADMA are effective inhibitors of NO and its regulated pathways. SDMA is not an inhibitor of NO and all three methylated arginines enter cells through cationic amino acid transporters known collectively as the y+ transporter which also transports arginine, lysine and ornithine (Bogle et al., Am. J. Physiol. (1995) 269:C750–C765). Such transport mechanism can result in over five-fold concentration of the methylarginines intracellularly as compared to extracellular concentration. The methylarginines interfere with the generation of NO and the transport of arginine and other cationic amino acids.

The language "arginine compound level" includes the amount or concentration of arginine compounds in a body sample. In an embodiment, the arginine compound level of the body sample is indicative of the concentration of arginine compounds in the body. Advantageously, the concentration of the arginine compound in the body can be extrapolated from the arginine compound level determined through the methods and kits of the invention. The invention includes methods and kits which detect the presence or absence of a arginine compound concentration over a certain threshold concentration, which may, advantageously, be adjusted based on the optimal or advantageous arginine compound concentrations for a particular situation or a particular patient (e.g., a patient with an NO related disorder or a cardiovascular disorder). For example, the certain threshold concentration of an arginine compound may be individual to a user or to a group of users, e.g., patients with cardiovascular disorders, etc. In another embodiment, the invention includes methods and kits which detect relative or absolute concentrations of arginine compounds in a body sample.

For example, the arginine compound level of ADMA and SDMA has been determined to be about 500 nM–1 µM in plasma of healthy humans. However, the arginine compound level of other arginine compounds (e.g., L-NMMA) has generally been found to be considerably lower. Methylarginines also are found in body fluids, such as urine, in at a concentration of about 60 µmol/24 hours (Macallister et al., Nephrol Dial. Transplant. (1996) 11:2449–2452).

However, aberrant levels of arginine compounds may either be used to either indicate the presence or the potential presence of an arginine compound associated disorder, e.g., such as a NO related disorder or another disorder characterized by concentration or amounts of arginine compounds in a body sample which can be detected using the methods and compositions of the invention. The term "arginine compound associated disorders" includes disorders or states which are characterized by the presence or absence of arginine compounds such as L-arginine, ADMA, SDMA, and/or L-NMMA. The term "NO related disorders" includes disorders which involve NO at some point of the pathway and which can be identified through the use of the methods and compositions of the invention. The term includes disorders which involve, for example, the L-arginine:NO pathway.

One example of an arginine compound associated disorder is renal failure. In renal failure, methylarginine excretion is diminished and both ADMA and SDMA accumulate in the plasma (Macallister et. al., *Br. J. Pharmacol.* (1996) 119:1533–1540). Ranges of 0.5–10 $\mu$M have been reported. The methods, compositions and kits of the invention could be used to identify the aberrant levels of ADMA and/or SDMA to help diagnose a patient's disorder.

Aberrant levels of arginine compounds in body samples also can be used to identify or help diagnose other arginine compound related disorders. Levels of ADMA and SDMA are higher in patients with renal failure, which falls post dialysis. High levels of ADMA in renal failure might include sodium handling, increased vascular tone and reactivity, enhanced atherogeneses and effects on immune functions. In children with hypertension levels of ADMA are increased and correlate positively with blood pressure and negatively with circulating levels of nitrogen oxides and NO adducts (Goonasekera et. al., *J. Hypertension* (1997) 15:901–909). Additionally, levels of ADMA were recently shown to correlate with increased presence of hyperlipidaemia in both animals and humans (Bode-Boger et. al., *Biochem. Biophys. Res. Commun.* (1996) 219:598–603; Boger et. al., *Circulation* (1998) 98:1842–1847). This finding suggested that ADMA levels might represent a novel risk factor for cardiovascular disease. Therefore, the use of the methods, kits and substances of the invention, e.g., arginine sensing and/or recognizing substances, could be used to readily identify patients at risk or suffering for arginine related disorders, such as cardiovascular disease.

Other arginine compound associated diseases which involve elevated levels of ADMA include Schizophrenia (Das et al., *Neurosci Lett.* (1996) 215:209–211), *H. pylori* infection of gastric mucosa (Fandriks et al., *Gastroenterology* (1997) 113:1570–1575), Alloxan-induced hyperglycaemia (Masuda et al., *Br. J. Pharmacol.* (1999) 126:211–218), thrombic microangiopathy (Herlitz et al., *Scand J. Urol. Nephrol.* (1997) 31:477–479), and atherosclerosis (Boger et al., *Circulation* (1997) 96:1282–1290; Miyazaki et al., *Circulation* (1999) 99:1141–1146). Therefore, in another embodiment, the methods, compositions and kits of the invention may be used to identify patients at risk or suffering from any one of these disorders or other disorders characterized by aberrant amounts of arginine compounds present in a body fluid.

Very low levels of NO inhibitors represented by the dimethylarginines have a broad spectrum of biological activities. Effects on the cardiovascular system have been described extensively. In human blood vessels L-NMMA at a concentration of 1 $\mu$M causes up to 20% inhibition of bradykinin-induced vasodilatation (Macallister *Kidney Int.* (1994) 45:737–742). In patients with septic shock, infusion of L-NMMA sufficient to increase the circulating levels of L-NMMA to 5 $\mu$M are associated with very substantial (over 70%) increases in vascular resistance and more modest (10–15%) increases in arterial blood pressure (Petros et al., *Cardiovascular Res.* (1994) 28:34–39). ADMA also produces biological effects at low concentrations and circulating concentrations in the order of 10 $\mu$M increase blood pressure by about 15% in guinea-pigs (Valiance et. al., *Lancet* (1992) 339:572–575). Significant effects of methylarginines on blood vessels probably occur at even lower concentrations, since it is clear that L-NMMA can increase systemic vascular resistance and lower cardiac output without producing major effects on arterial pressure. Low doses of L-NMMA (1 mg/kg) decreases renal blood flow and affects sodium handling in humans but blood pressure is not affected. Low levels of NOS inhibitors may produce chronic effects. In cholesterol fed rabbits, doses of NOS inhibitors that do significantly affect arterial blood pressure, markedly enhance neointima formation and early atherogenesis (Cayatte et al., *Arterioscler. Thromb.* (1994) 14:753–759). These data indicate that minor degrees of inhibition of NOS can lead to significant biological effects that might have implications for long-term homeostasis of the cardiovascular system.

In one embodiment, the arginine compound level is the arginine level, the L-NMMA level, the SDMA level, the ADMA level or a combination thereof.

The term "arginine level" refers to the level, amount, or concentration of arginine in the body sample. Similarly, the term "L-NMMA level" refers to the level, amount or concentration of L-NMMA in the body sample. The terms "SDMA level" and "ADMA level" refer to the level, concentration, or amount of SDMA or ADMA in a body sample, respectively.

The term "arginine sensing substance" includes substances which interact with arginine compounds, such that arginine compounds levels in a body sample can be determined. Advantageously, the determination of the arginine compound level is discernible without the use of laboratory equipment. For example, in an advantageous embodiment, the arginine sensing substance interacts with the arginine compound in a body sample such that the arginine compound level can be determined visually, e.g., by a change in color, hue or intensity of the mixture of the body sample and the arginine sensing substance. The term "laboratory equipment" includes HPLC, fluorometers, spectrometers (NMR, IR), optical density meters, etc. The term "laboratory equipment" does not include charts or other tables which involve visual comparison of a solution to the chart or table, equipment (e.g., refrigerator, freezer, scissors) usually found in a home, or equipment, e.g., a solution vial, dish, or a syringe, which can be reasonably packaged with the kit without prohibitive expense to the user or another.

The term "interact" or "interactions" include events which allow for the detection of arginine compounds in a sample. In an embodiment, the term includes electrostatic or hydrogen bonding interactions between the arginine compound recognizing substance and the arginine compound in the sample. In a further embodiment, the interactions are specific for a particular arginine compound.

In other embodiments, the determination of arginine compound levels include additional steps, such as, exposing the mixture to radiation of appropriate wavelength to observe fluorescence. Furthermore, additional substances may be used to detect the presence of an interaction between the arginine sensing substance and a arginine compound. Preferably, the arginine sensing substance interacts specifically with L-arginine, L-NMMA, ADMA, SDMA, or another arginine analog which is indicative of an arginine compound associated disorder or a disorder of the L-arginine NO pathway. In one embodiment, the arginine sensing substance comprises a polypeptide, e.g., an antibody or a fragment thereof, which binds to the arginine compounds. In another embodiment, the arginine sensing substance comprises a cage molecule, such as, for example, a fullerene. Advantageously, the arginine sensing substance specifically interacts with a specific arginine compound, for example, L-arginine, L-NMMA, ADMA, or SDMA. For example, a L-arginine sensing substance may interact specifically with L-arginine to indicate the L-arginine level in a body sample. Similarly, an ADMA sensing substance would interact specifically with ADMA to indicate the ADMA level in a body sample. Furthermore, one or more sensing substances may be used in combination to specifically detect several arginine compounds separately. Furthermore, the term "arginine sensing substances" includes "arginine compound "recognizing substances."

The term "arginine compound recognizing substances" includes substances which specifically interact with arginine compounds. The arginine compound recognizing substances may be specific for certain arginine compounds, e.g., L-arginine (e.g., "L-arginine recognizing substances"), L-NMMA (e.g, "L-NMMA recognizing substances"), ADMA (e.g., "ADMA recognizing substances"), or SDMA (e.g., SDMA recognizing substances") or salts or ions thereof. The interaction of arginine compounds with arginine compound recognizing substances can be detected without modification of the arginine or arginine compound, or the production of an enzymatic product. However, deprotonation or protonation of acidic or basic groups of arginine compounds is not considered to be modification of the arginine compounds.

Arginine compound recognizing substances involve specific interactions between the substances and the arginine compounds. The language "specifically interact" or "specific interactions" is not intended to include general methods of separation and detection, such as chromatographic techniques (e.g., HPLC) which use, for example, molecular weight, charge, or vaporization point to separate molecules with similar physical properties. The language "specifically interact" or "specific interactions" includes interactions between the arginine compound recognizing substance and the arginine compound which are capable of identifying the arginine compound based on its structural properties on a molecular level, such as the size, location and polarity of chemical moieties of the arginine compound. Furthermore, the term "arginine compound sensing substances" includes "arginine compound recognizing substances." In a preferred embodiment, the arginine compound recognizing substance specifically interacts with arginine, L-NMMA, ADMA, or SDMA.

Examples of arginine compound recognizing substances include, for example, antibodies which detectably interact with arginine compounds and other organic and organometallic molecules.

In a preferred embodiment, the arginine compound recognizing substance is an organic small molecule. The term "organic small molecule" includes organic and organometallic molecules. In one embodiment, the organic small molecules of the invention interact with arginine compounds such that the presence or concentration of arginine compounds in a sample can be determined.

In one embodiment, the arginine compound recognizing substance is an organic small molecule which specifically interacts with arginine compounds, such as L-arginine, L-NMMA, ADMA, SDMA, etc. These compounds can be synthesized and designed using the techniques and design strategy of "host-guest" chemistry, in which a receptor is designed to the specification of the "guest" (e.g., the arginine compound.) Examples of the methods for designing hosts (recognizing substances) can be found in U.S. Pat. Nos. 5,030,728, and 5,128,466.

Over the past 30 years, chemists have designed and synthesized many organic compounds capable of interacting with other organic molecules. These organic compounds are also termed "host" compounds or "artificial receptors" by analogy with biological receptors that bind and recognize "guests." "Host-guest" or supramolecular chemistry, has numerous biomedical applications, including detection and quantitation of analytes, such as arginine compounds, in biological fluids. In one embodiment, the invention includes "host" arginine sensing substances which interact with arginine compounds.

For example, "host-guest" supramolecular chemistry has been used to create diketone "hosts" which interact with urea "guests" (Bell, T. W. et al. *J. Am. Chem. Soc.* (1988) 110:3673–3674). The strength of this complex was thought to be due to the relative rigidity of the diketone "host" prior to interaction with the urea, and the position of the diketone's hydrogen-bond acceptor nitrogen and oxygen atoms in nearly ideal locations to form strong hydrogen bonds with the arginine compound's NH stabilizing groups. The principle of preorganization includes both the effect of the conformational organization of the host and the low solvation of the binding site before complexation (Cram, D. J. *Angew. Chem. Int. Ed. Engl.* (1986) 25:1039–1134). Other series of highly preorganized hydrogen bonding receptors for various guest molecules have been also synthesized and discussed (Bell, T. W. et al. *Angew. Chem. Int. Ed. Engl.* (1997) 36:1536–1538; Bell, T. W. et al. *Angew. Chem. Int. Ed. Engl.*, (1990) 29:923–925; Beckles, D. L. et al. *Tetrahedron* (1995) 51:363–376; U.S. Pat. Nos. 5,030,728; and 5,283,333).

Arginine compound recognizing substances, e.g., organic small molecules, designed to interact with arginine compounds and, advantageously, signal this interaction may be used to determination of the arginine compound levels in body samples.

One example of a the hexagonal lattice approach to a water-soluble arginine receptor, the "arginine cork" is shown in Scheme 1 (Bell et al., *Angew. Chem., Int. Ed. Engl.*, 1999, 38, 2543–2547). Arginine compound recognizing substance (1) interacts with alkylguanidinium ions, the side chain of arginine, in water with formation of a complex, with arginine. The dissociation constant of the complex of 1 with arginine in water was found to be 1.1 mM. Electrostatic attraction between negatively charged carboxylate groups of 1 and the positive charge of the guanidinium ion together with the preorganized network of hydrogen-bond acceptor sites of the receptor make the complex of 1 with guanidinium ion to be highly stable. However, receptor 1 binds any alkylguanidinium compounds and lacks recognition specificity, which is important for selective sensor.

Scheme 1

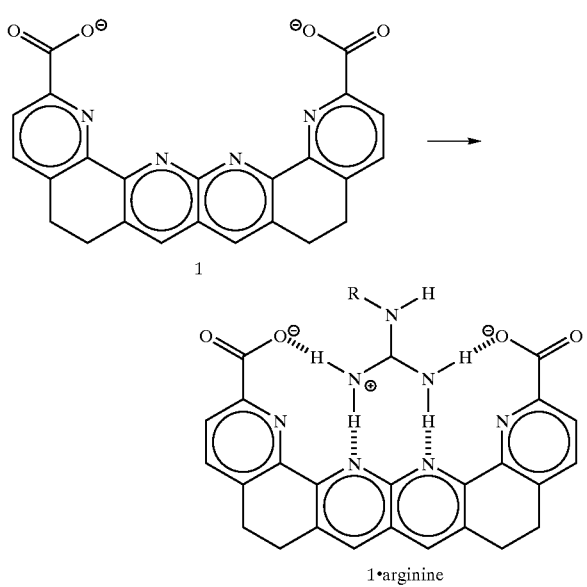

1·arginine

In another example, a rigid U-shaped guanidinium receptor (2) (Scheme 2) changes its light absorption properties upon complexation to unsubstituted guanidinium ion (Bell et al., *Angew. Chem. Int. Ed. Eng.* 1990, 29, 923–925). Receptor 2 is restricted by design to bind only to unsubstituted guanidinium ion.

Scheme 2

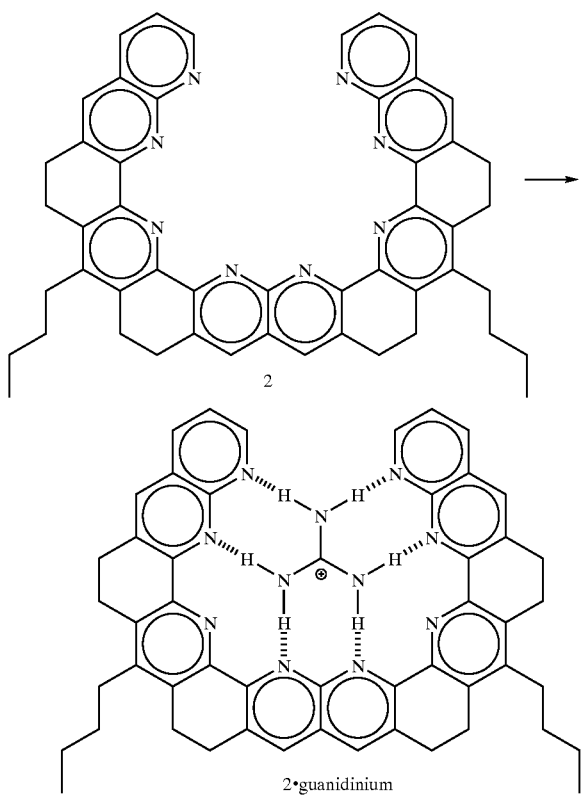

2·guanidinium

The invention pertains, at least in part, to a series of arginine compound recognizing substances designed to interact with arginine compounds selectively, e.g., by utilization of complementary electrostatic and preorganized hydrogen-bonding interactions. In one embodiment, the arginine compound recognizing substances of the invention are of the formula (I):

$$G(N)_n(C)_m \qquad (I)$$

wherein

G is a guanidinium recognizing moiety;
N is an ammonium recognizing moiety;
C is a carboxylate recognizing moiety; and
n and m are each independently integers from 0 to 10.

Generally, arginine has several functional groups, guanidinium, ammonium and carboxylate, which may be targeted for recognition. In an embodiment, the arginine compound recognizing substances comprises a guanidinium recognizing moiety (G), an ammonium recognizing moiety (N), and a carboxylate recognizing moiety (C). The arginine compound recognizing substance may also further comprise linking moieties which connect the guanidinium recognizing moiety, the ammonium recognizing moiety, and the carboxylate recognizing moiety.

In an embodiment, the arginine compound recognizing substances have the general structure shown in Scheme 3.

Scheme 3

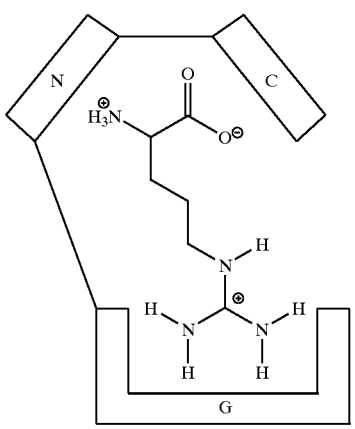

The term "guanidinium recognizing moiety" ("G") includes moieties which coordinate with arginine compounds. In an embodiment, the moiety interacts with the guanidinium moiety of the arginine compound. Preferably, the guanidinium recognizing moiety detectably coordinates with the arginine compounds at biological concentrations. In an embodiment, the guanidinium coordinating moiety is multicyclic, and may advantageously contain at least one heterocycle, e.g., a nitrogen containing heterocycle, e.g., a pyridyl moiety. In an embodiment, the guanidinium recognizing moiety is hydrogen-bond accepting and/or anionic.

The guanidinium recognizing moiety may be designed such that it specifically recognizes non-methylated guanidinium group of arginine (e.g. a "non-methylated guanidinium recognizing moiety"), the monomethylated guanidinium group of NMMA (e.g, a "monomethylated guanidinium recognizing moiety"), the symmetric dimethylation of the guanidinium group of SDMA (e.g. a "symmetric dimethylated guanidinium recognizing moiety") or the asymmetric guanidinium group of ADMA (e.g., an "asymmetric dimethylated guanidinium recognizing moiety", "Q"). The term "guanidinium recognizing moiety" includes each of these recognizing moieties (e.g. non-methylated guanidinium recognizing moiety, monomethylated guanidinium recognizing moiety, and the symmetric and asymmetric guanidinium recognizing moieties.)

Examples of non-methylated guanidinium recognizing moieties for arginine recognizing substances include the following structures shown below.

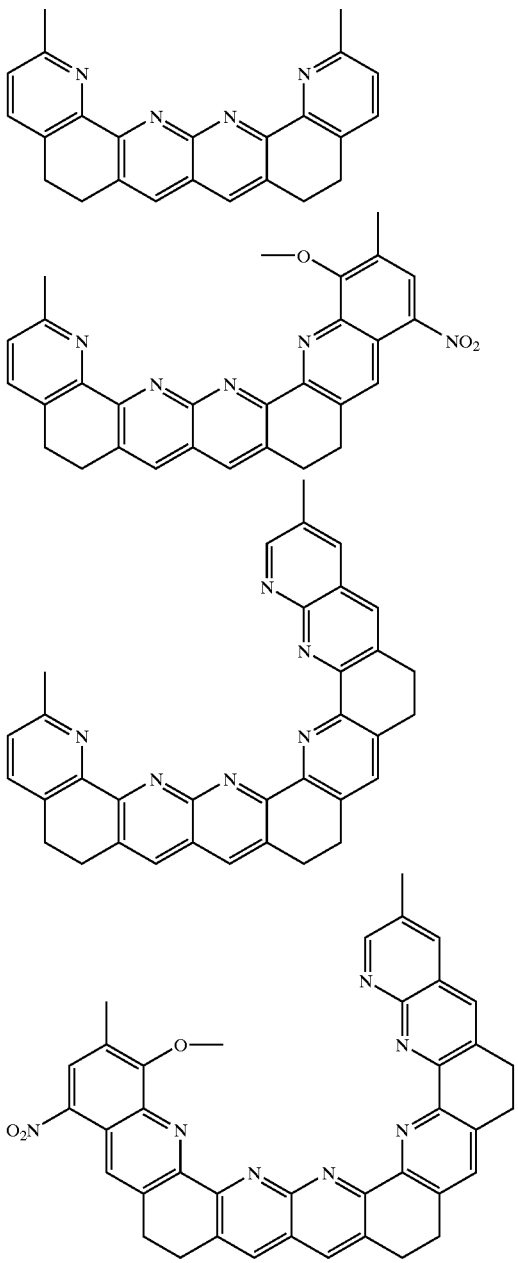

Furthermore, other examples of guanidinium recognizing moieties include derivatives and analogs of the guanidinium recognizing moieties shown above. For example, the guanidinium recognizing moieties shown above can be substituted with various functional groups to enhance their ability to perform their function, e.g., detect arginine compound levels. Analogs include, for example, compounds and moieties which are structurally similar but may have substitutions of heteroatoms or other changes which do not prohibit the guanidinium recognizing moiety or the arginine compound recognizing substance from performing its intended function, e.g., determine arginine compound levels in a body sample. In an advantageous embodiment, the analogs or derivatives of the guanidinium recognizing moieties shown above enhance the ability of the arginine compound recognizing substance to perform its intended function.

The term "asymmetric dimethylated guanidinium recognizing moiety" or "Q" comprises moieties which are capable of interacting with the dimethylguanidinium group such as, for example, rigid heteroaromatic coordinating moieties, such as those shown below:

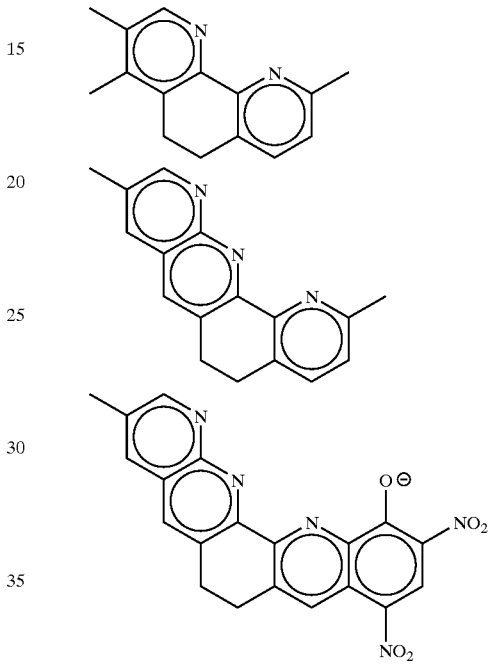

The coordinating moiety can be neutral, anionic, or linked to an anionic group, such as carboxylate or phosphate.

The term "ammonium recognizing moiety" ("N") includes moieties which interact with the ammonium moiety of the arginine compound, such that arginine compound recognizing substance of the invention is capable of performing its intended function, e.g., detect arginine compounds. In a further embodiment, the ammonium recognizing moiety is a neutral or anionic groups and may contain heteroatoms such as nitrogen and oxygen. Examples of ammonium recognizing moieties include, but are not limited to, carbonyl, amide, hydroxyl, hydroxime, carboxylate, ether, ester, pyridine, pyrimidine, phenolate, phosphate, and combinations thereof. Ammonium recognizing moieties may comprise one or several interlinked groups. Some examples of ammonium recognizing moieties are shown below:

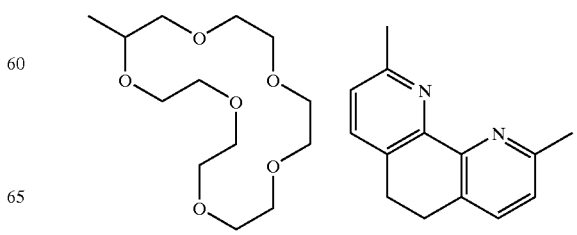

-continued

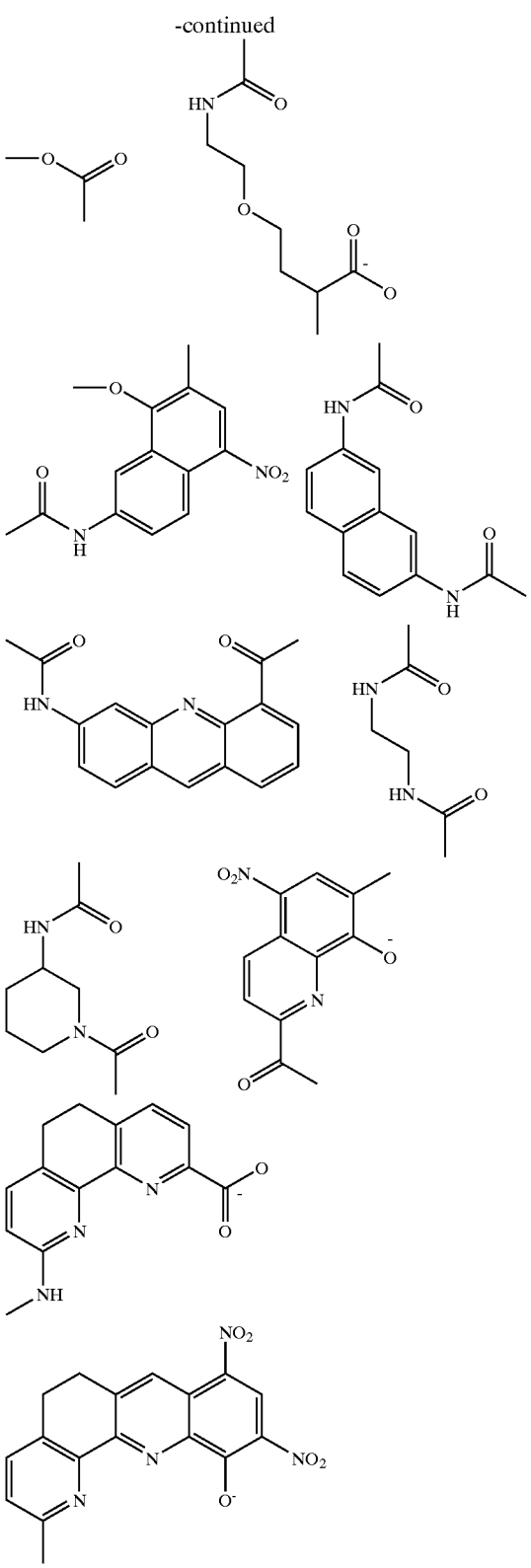

Analogs and derivatives of the ammonium recognizing moieties mentioned above are also included.

The term "carboxylate recognizing moiety" ("C") includes moieties which are capable of interacting with carboxylate moiety of the arginine compound, such that the arginine compound of the invention is capable of performing its intended function. Examples of carboxylate recognizing moieties include neutral and cationic groups. In a further embodiment, the carboxylate recognizing moiety comprises a cationic group, e.g., a guanidinium or ammonium ion, optionally linked to additional hydrogen-bond donating groups such as amine, amide, hydroxyl, hydroxime or a substituted urea. Examples of carboxylate recognizing moieties include but are not limited to:

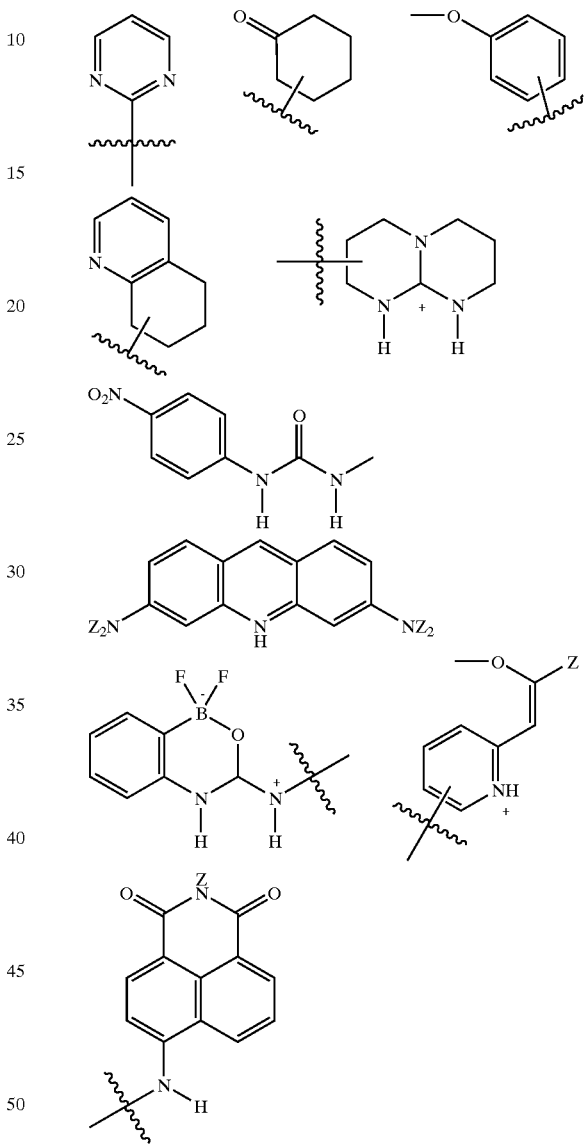

wherein Z is alkyl, alkenyl, alkynyl, hydrogen, acyl, hydrogen, and halogen atoms. Analogs and derivatives of the carboxylate recognizing moieties mentioned above are also included.

The term "linking moiety" includes moieties which connect (e.g., through covalent bonds) the guanidinium recognizing moiety or the dimethylguanidinium recognizing moiety, the ammonium recognizing moiety, and the carboxylate recognizing moiety. The linking moiety may be a chain of 1 to 30 atoms, optionally substituted, and may contain rings, heteroatoms, single, double, and triple bonds. Advantageously, the linking moiety allows the arginine compound recognizing substance to perform its intended function, e.g., detect arginine compounds.

The arginine compound recognizing substances comprise any combination and order of moieties G, A and C. The combination of moieties G, A, and C can be arranged in linear or cyclic fashion. Some examples of arginine recognizing substances are shown below:
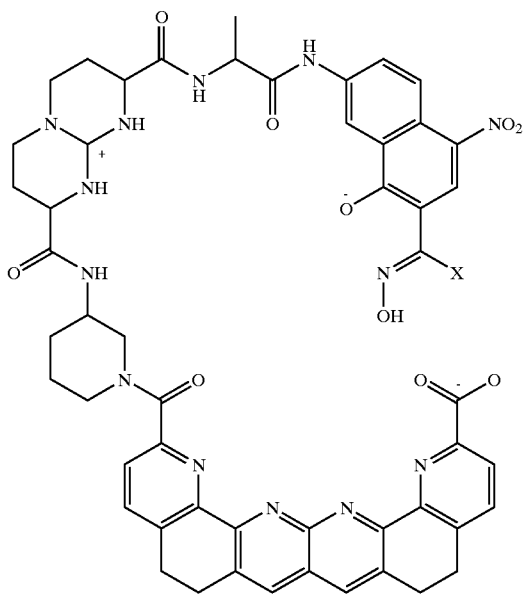
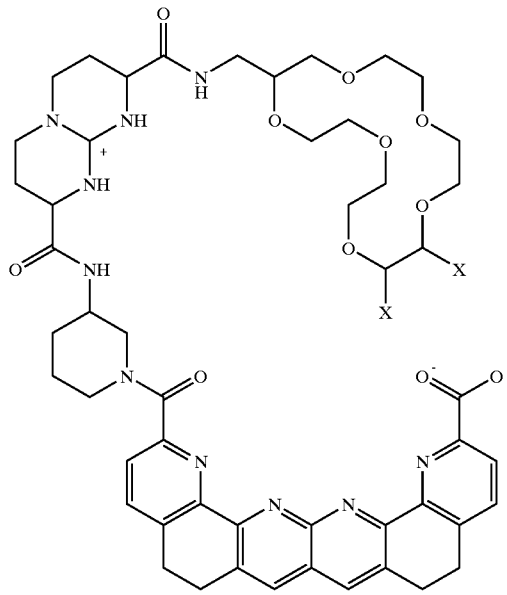
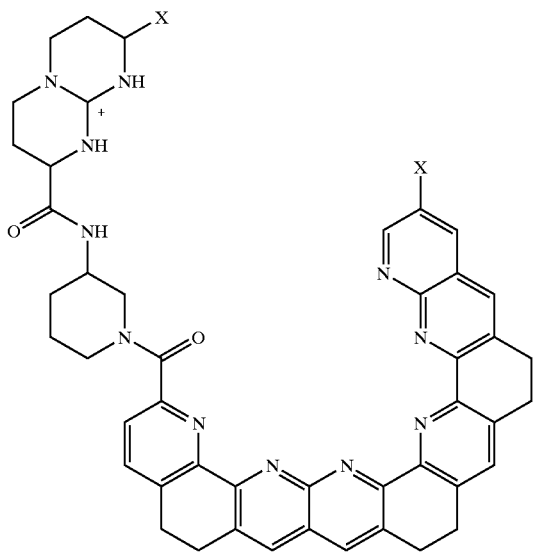
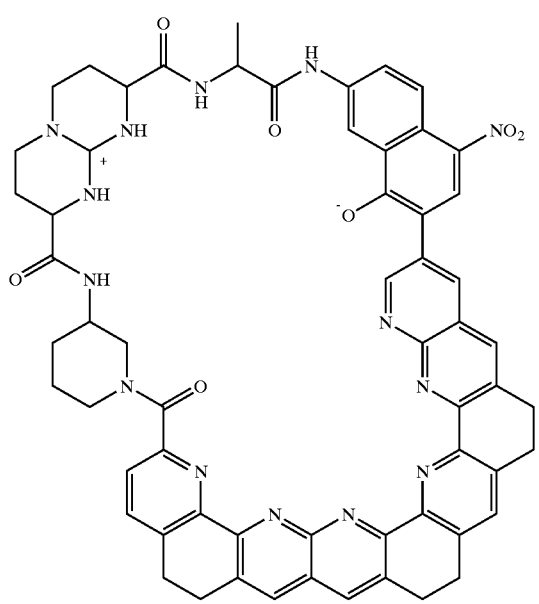

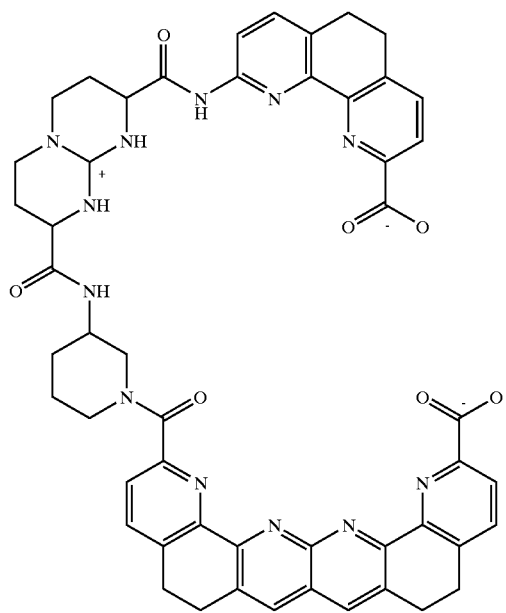
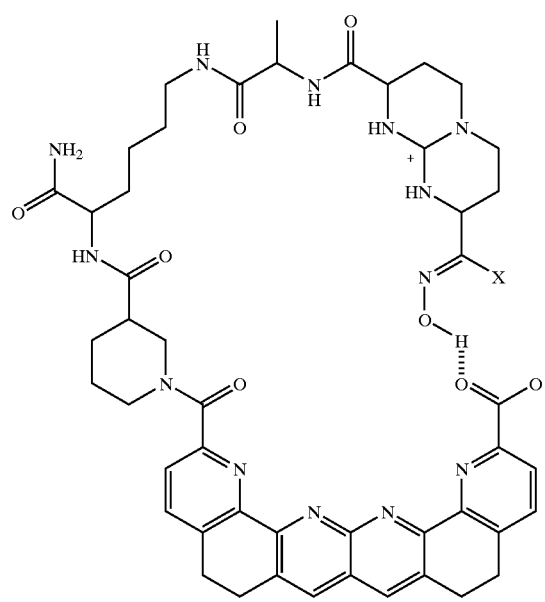
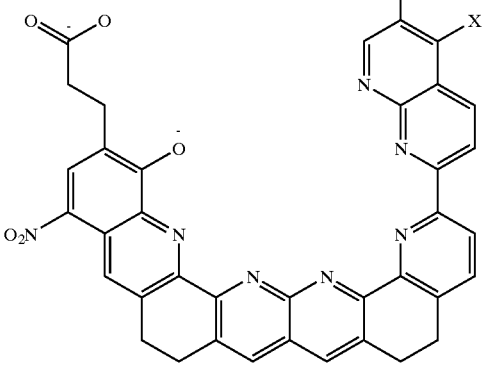
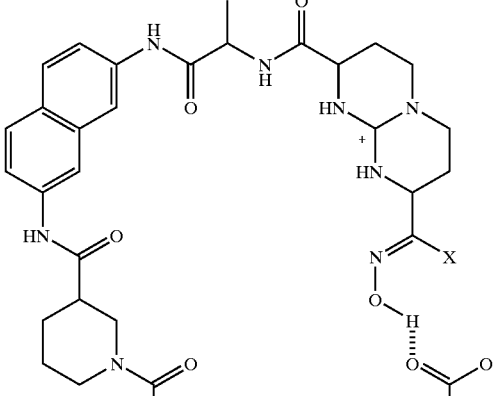
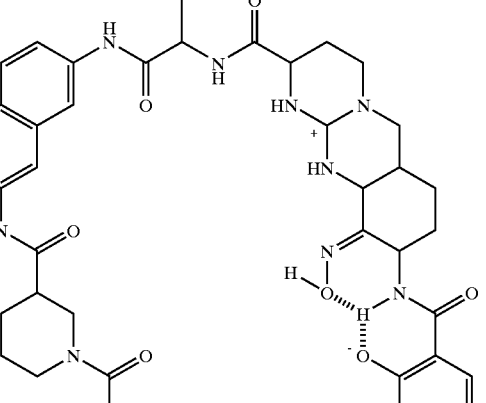

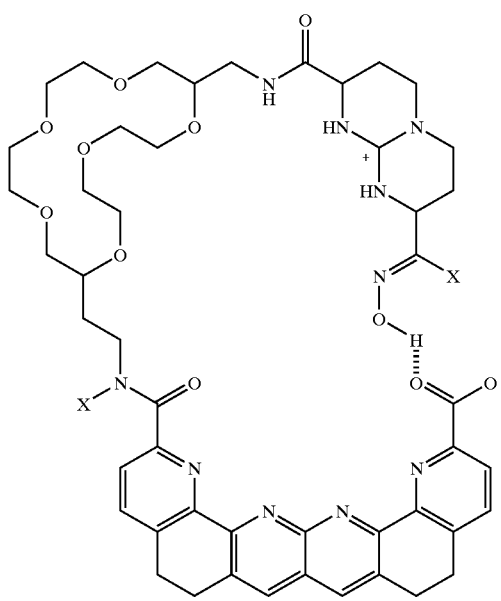
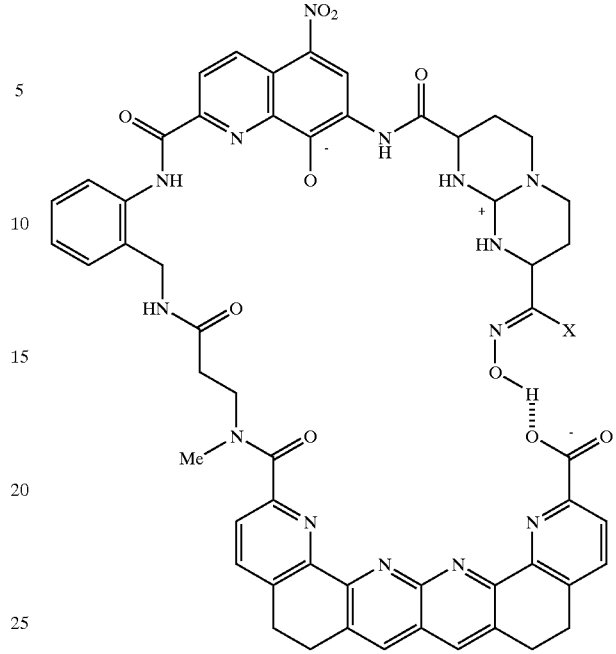
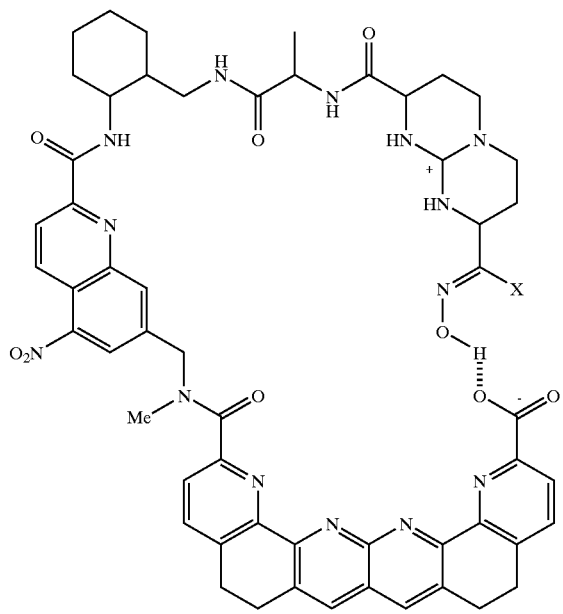
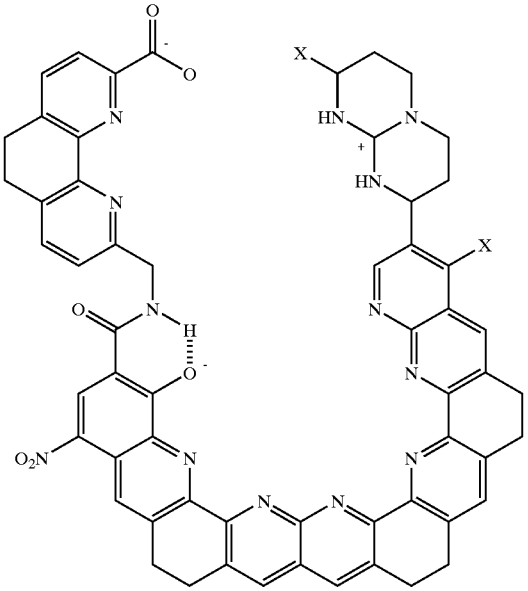

-continued

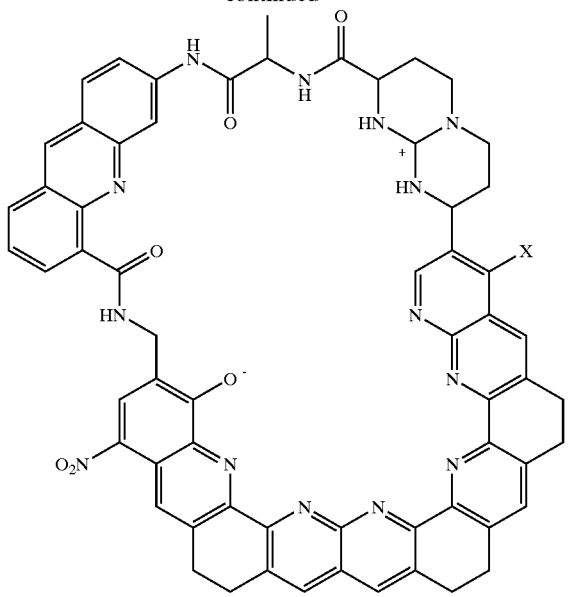

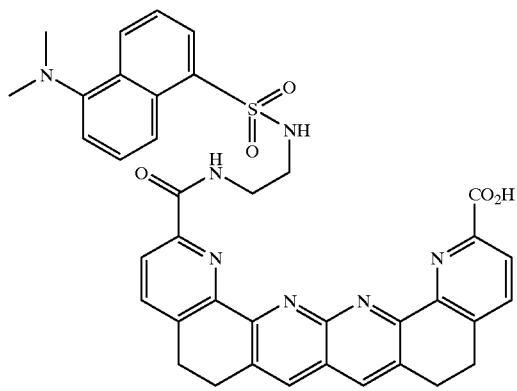

wherein X is hydrogen, alkyl, alkenyl, alkynyl, aryl, halogen, a chromophore, or a fluorophore. Analogs and derivatives of the arginine recognizing substances mentioned above are also included.

In one embodiment, the arginine sensing substances and the arginine compound recognizing substances of the invention do not include the compounds described in Bell et al., Angew. Chem., Int. Ed. Engl., 1999, 38, 2543–2547.

In one embodiment, the chromophore may be incorporated into the interaction site of the arginine compound on the arginine compound recognizing substance. In one embodiment, the design of arginine compound recognizing substance which changes its optical properties upon com plexation of arginine compound of interest. The inclusion of a chromophore or fluorophore may advantageously enhance communication between interaction of the arginine compound with the arginine recognizing substance (Chemosensors of Ion and Molecule Recognition, J. P. Desvergne, A. Czarnik, Eds., Kluwer:Dordrecht, The Netherlands, 1997, pp.121–132).

In another embodiment, the arginine compound recognizing substance is an "ADMA recognizing substance" which is capable of detectably interacting with ADMA, preferably, specifically. In an embodiment, the ADMA recognizing substances interact specifically with ADMA, e.g., using complementary electrostatic and/or preorganized hydrogen-bonding interactions. ADMA has several distinct groups, dimethylguanidinium, ammonium and carboxylate, which may be targeted for recognition. In an embodiment, the ADMA recognizing substance is of formula (II):

$$Q(N)_n(C)_m \qquad (II)$$

wherein

Q is an asymmetric dimethylated guanidinium recognizing moiety;

N is an ammonium recognizing moiety;

C is a carboxylate recognizing moiety, and n and m are each independently integers from 0 to 10.

In an embodiment, the ADMA recognizing substance comprises at least one asymmetric dimethylated guanidinium recognizing moiety Q, at least one ammonium recognizing moiety N, and at least one carboxylate recognizing moiety C. The ADMA recognizing substance may also further comprise linking moieties which connect the dimethylguanidinium recognizing moiety, ammonium recognizing moiety, and the carboxylate recognizing moiety. In one embodiment, the ADMA recognizing substance is represented by the Q-C-N structure in the scheme shown below:

Scheme 4

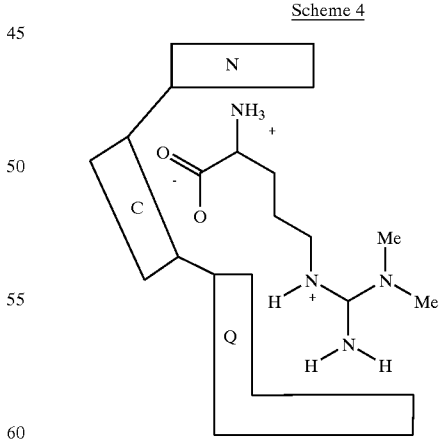

The ADMA recognizing molecules consist of any combination and order of moieties Q, A and C. The combination of moieties Q, A, and C can be arranged in linear or cyclic fashion. Some examples of ADMA recognizing substances are shown below:

23
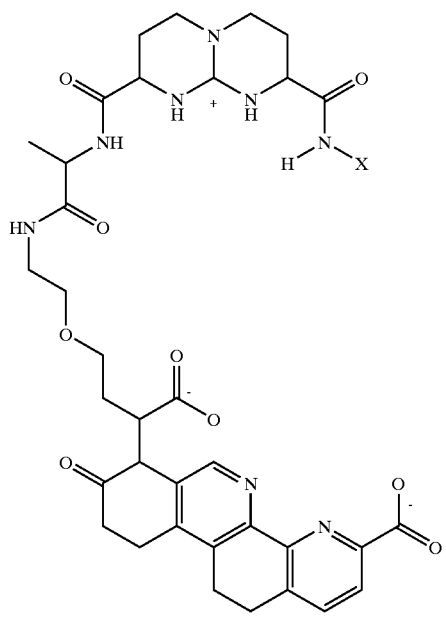
24
-continued
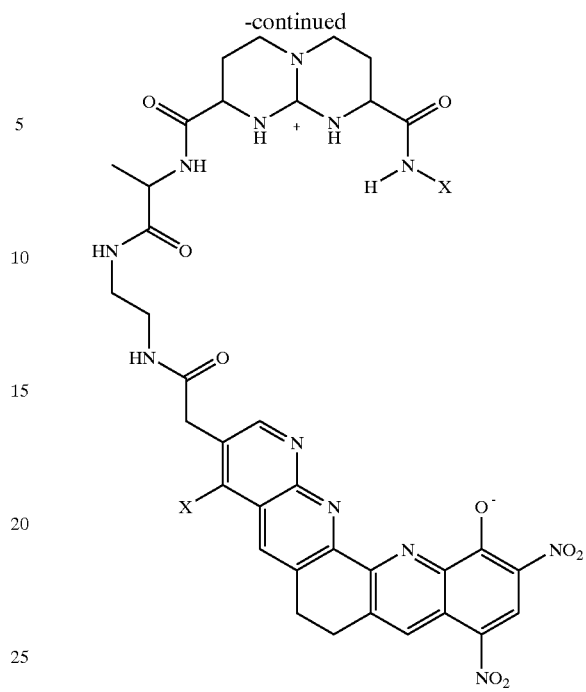
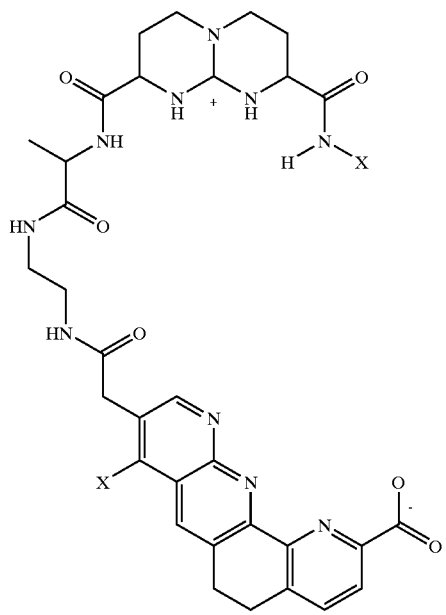
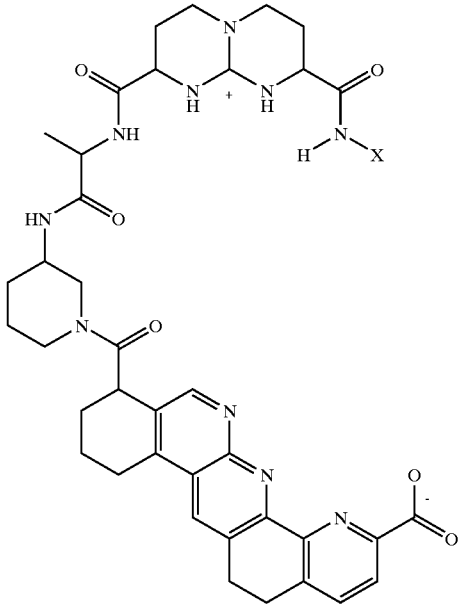

25
-continued
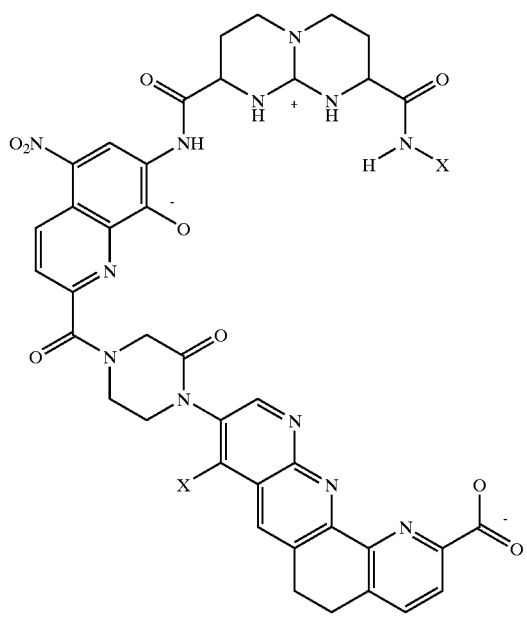
26
-continued
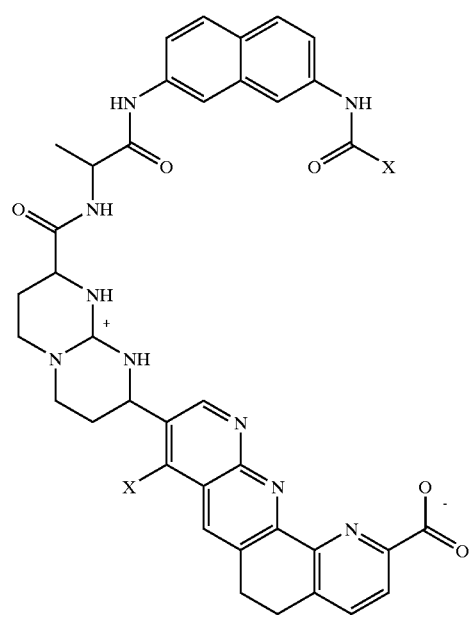
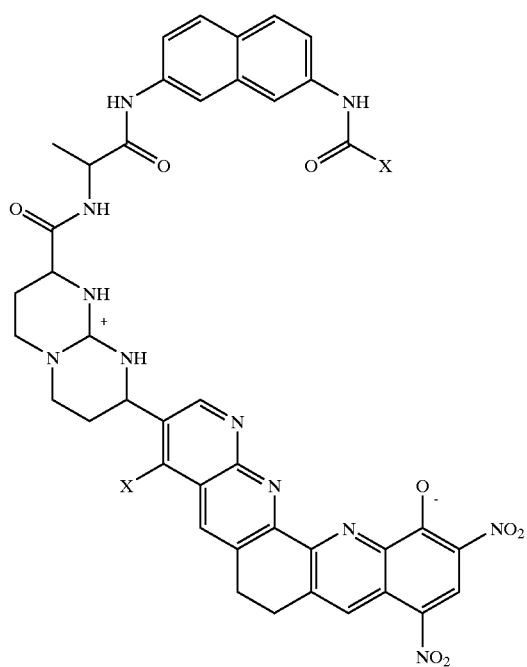

-continued

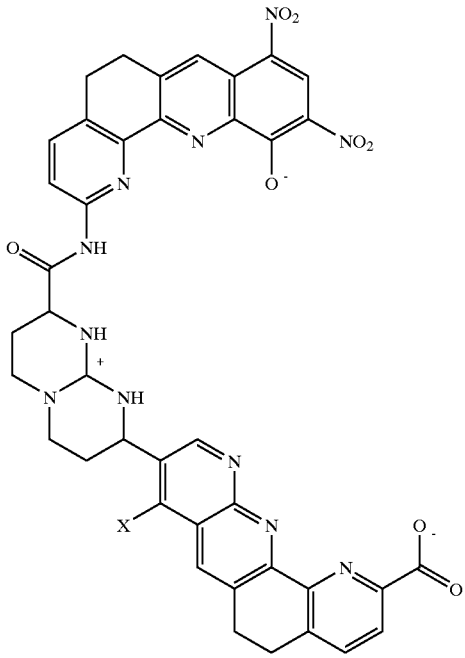

wherein X is hydrogen, alkyl, alkenyl, alkynyl, aryl, halogen, chromophore or a fluorophore. Analogs and derivatives of the ADMA recognizing substances mentioned above are also included.

The invention also pertains, at least in part, to the arginine compound recognizing substances described herein per se, as well as kits, packages and other products which comprise the arginine compound recognizing substances described herein.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to five carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

The term "substituted" includes substituents mentioned above, which include halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

In one embodiment, the levels of the arginine compound can be directly analyzed visually, e.g., by a change in color of the arginine sensing substance and arginine compound mixture.

In one embodiment of the invention, the color, intensity or hue of the arginine sensing substance or a product thereof may be calibrated to indicate a range of arginine compound levels (e.g., the intensity of the color of the arginine sensing substance may intensify as the arginine compound level in the sample is increased; the color or hue of the arginine sensing substance may change as the arginine compound level is decreased.) In a further embodiment, the resulting mixture is analyzed by comparing the color, hue or intensity of the resulting mixture with a calibrated scale, which indicates arginine compound level in the body fluid, or, preferably, in the body. In a further embodiment, the intensity of the color can be determined quantitatively, for example, by measuring changes in the optical density of a solution or by measuring the fluorescence emission.

The term "color" includes changes in the absorbance or emission radiation in the ultraviolet, visible, or infrared spectrum. Advantageously, the change in color is a change in the visible color of the arginine sensing substance. Alternatively, the change in color could be a change in the wavelength of fluorescence. Furthermore, the level of fluorescence, color or optical change may be quantified, using known spectroscopic (e.g., fluorimetric, colorimetric) techniques.

Examples of arginine compound recognizing substances include molecules capable of specifically interacting with arginine compounds with potentially useful changes in color, light absorption intensity or wavelength, or fluorescence emission intensity or wavelength. Such optical effects can be produced, for example, by rearrangement, transprotonation, ionization, deionization, conformational change, polarization, solvation change or electronic interaction between the arginine compound recognizing substance and the arginine compound. The arginine compound recognizing substances can be designed in a manner similar to that used to design other compounds which are known to generally interact with guanidinium compounds (Bell, T. W. et al. *Angew. Chem. Int. Ed.*, (1999) 38, 2543–2548).

In one embodiment, arginine compound recognizing substances of the invention can be designed advantageously to produce an optical signal, in addition to binding a arginine compound of interest with high affinity. This signal can be, for example, a change in light absorption or emission resulting from a structural change of the arginine compound recognizing substance, electronic polarization of the arginine compound recognizing substance, or other electronic interaction between the compound of interest and the arginine compound recognizing substance.

In a further embodiment, the interaction between the arginine sensing substance and the arginine compound can be detected through the use of fluorescence emission. Quenching or enhancement of emission intensity can result from energetically undemanding processes, such as electronic interaction between arginine sensing substance and the arginine compound of interest or changes in solvation of either substance upon complexation.

In a further embodiment, the method also comprises the step of administering a therapeutically effective amount of a arginine compound to increase arginine compound levels in a subject from which the body fluid sample was taken.

The term "administering" includes routes of administration which allow the arginine compound to perform its intended function. Examples of routes of administration which can be used include parental injection (e.g., subcutaneous, intravenous, and intramuscular), intraperitoneal injection, oral, inhalation, and transdermal. The injection can be bolus injections or can be continuous infusion. Depending on the route of administration, the arginine compound can be coated with or disposed in a selected material to protect it from natural conditions which may detrimentally effect its ability to perform its intended function. The arginine compound can be administered alone or with a pharmaceutically acceptable carrier. Further, the arginine compound can be administered as a mixture of arginine compounds, which also can be coadministered with a pharmaceutically acceptable carrier. Preferably the arginine compounds are administered orally.

The phrase "pharmaceutically acceptable carrier" includes pharmaceutically acceptable materials, compositions or vehicles, such as a liquid or solid filler, diluent, excipient, solvent or encapsulating material, involved in carrying or transporting a compound(s) of the present invention within or to the subject such that it can performs its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The language "therapeutically effective amount" includes the amount of the arginine compound sufficient to prevent onset of diseases or significantly reduce progression of such diseases in the subject being treated. A therapeutically effective amount can be determined on an individual basis and will be based, at least in part, on consideration of the severity of the symptoms to be treated and the activity of the specific analog selected if an analog is being used. Further, the effective amounts of the arginine compound may vary according to the age, sex and weight of the subject being treated. Thus, a therapeutically effective amount of the arginine compound can be determined by one of ordinary skill in the art employing such factors as described above using no more than routine experimentation in clinical management. This therapeutic amount will be linked to levels of arginine compound detected in the assay kit proposed in this invention.

In another embodiment, the invention features a portable kit for determining arginine compound levels in a body fluid. In one embodiment, the kit comprises a arginine sensing substance and instructions for use. The kit may also include a container, vials for the bodily fluids, solvents, and arginine compounds in therapeutically effective amounts.

Although methods for determining arginine levels are currently available, generally these methods are not suitable for use in a kit, because they depend the extensive use of laboratory equipment.

In a preferred embodiment, the arginine sensing substance is associated with a solid support, e.g., embedded in a carrier matrix. Advantageously, the carrier matrix is insoluble in water and other physiological fluids. Examples of carrier matrices include: paper, sponge materials, cellulose, wood, woven and nonwoven fabrics, glass fiber, polymeric films, preformed and microporous membranes, synthetic and modified naturally-occurring polymers, or hydrophilic inorganic powders.

In a further embodiment, the solid support is a arginine compound sensing substance embedded test strip. The test strip may include a support strip, or handle, normally constructed from a hydrophobic plastic, and a reagent test region, containing a bibulous or a nonbibulous carrier matrix incorporating the arginine sensing substance. In one embodiment, the carrier matrix is an absorbent material that allows the body fluid to move, in response to capillary forces, through the carrier matrix to contact the arginine sensing substance and produce a detectable or measurable color transition. In the assay of a whole blood sample, the carrier matrix generally is not permeable to the cellular material. Therefore, the highly-colored cells can be wiped or blotted from the test pad and not interfere with or mask the assay for the arginine compound. Furthermore, if the carrier matrix is permeable to the cellular material, persons of ordinary skill in the art are aware of techniques and devices to separate the cellular material from the test sample to eliminate the interfering affects of the cellular material.

The carrier matrix can be any substance capable of incorporating the arginine sensing substances, as long as the carrier matrix is substantially inert, and is porous or absorbent relative to the soluble components of the liquid test sample. The expression "carrier matrix" refers to either bibulous or nonbibulous matrices that are insoluble in water and other physiological fluids and maintain their structural integrity when exposed to water and other physiological fluids. Suitable bibulous matrices include filter paper, sponge materials, cellulose, wood, woven and nonwoven fabrics and the like. Nonbibulous matrices include glass fiber, polymeric films, and preformed or microporous membranes. Other suitable carrier matrices include hydrophilic inorganic powders, such as silica gel, alumina, diatomaceous earth and the like; argillaceous substances; cloth; hydrophilic natural polymeric materials, particularly cellulose material, like celulosic beads, and especially fiber-containing papers such as filter paper or chromatographic paper; synthetic or modified naturally-occurring polymers, such as crosslinked gelatin, cellulose acetate, polyvinyl chloride, polyacrylamide, cellulose, polyvinyl alcohol, polysulfones, polyesters, polyacrylates, polyurethanes, crosslinked dextran, agarose, and other such crosslinked and noncrosslinked water-insoluble hydrophilic polymers. The carrier matrix can be of different chemical compositions or a mixture of chemical compositions. The matrix also can vary in regards to smoothness and roughness combined with hardness and softness.

The contents of all references and published patents and patent applications cited throughout the application are hereby incorporated by reference.

EXEMPLIFICATION OF THE INVENTION

EXAMPLE 1

Synthesis of Arginine Compound Recognizing Substance A (ACRSA)

This example is a synthesis of a sample arginine compound recognizing substance (ACRSA). Other compounds of the invention can be synthesized by other methods described herein and/or by consulting the chemical literature.

$^1$H and $^{13}$C NMR spectra were measured on a General Electric QE-300 NMR spectrometer operating at 300 and 75 MHz, respectively. Chemical shifts were referenced to the residual protonated solvent.

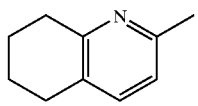

2-Methyl-5,6,7,8-tetrahydroqunoline (2)

A 1 L high pressure heavy wall Parr bottle was charged with quinaldine (1, 52.4 g, 0.366 mol) and cooled to 0° C. Then TFA (200 mL) was added at the same temperature. The yellow precipitate formed. After the salt was dissolved into TFA, 10% Pd on carbon (6.4 g) was added and the flask was attached to a high-pressure Parr hydrogenation instrument. The entire system was evacuated by water aspirator and then filled with hydrogen gas. The evacuation/filling procedure was repeated three more times. Then the system was filled with hydrogen at high pressure (45–50 psi) and shaker was activated. The bottle was shaken at room temperature for 3 days until hydrogen consumption stopped. The remaining pressure was carefully released and the catalyst was removed by vacuum filtration through Whatman No.2 filter paper and washed with water. The acidic solution was basified with NaOH pellet to pH 10~11 at room temperature. The product was extracted with hexane (100 mL×3). The combined hexane extracts were washed with water (50 mL×2) and brine (100 mL×1) and dried over $Na_2SO_4$. Removal of the solvent in vacuo gave tetrahydroquinoline 2 (81.9 g, 98%) as a brown oil. Physical data see A. B. Khasanov's Ph. D. Thesis, University of Nevada at Reno (2000), incorporated herein by reference.

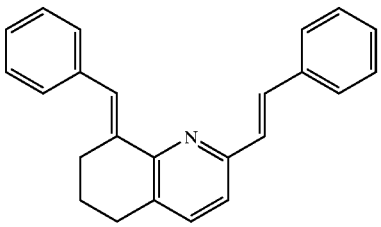

8-Benzylidene-2-styryl-5,6,7,8-tetrahydroquinoline (3)

A 1 L round-bottomed flask equipped with a stirring bar, condenser and nitrogen gas inlet was charged with 2-methyl-5,6,7,8-tetrahydroquinoline (2, 80.5 g, 0.547 mol), PhCHO (222 mL, 2.19 mol), and $Ac_2O$ (206 mL, 2.19 mol). The mixture was heated under reflux at 160–170° C. under nitrogen atmosphere for 5 days. Then all volatile materials were removed by distillation under atmospheric pressure at ~170° C. The residue was mixed with hot EtOH (200 mL) and stirred at 70° C. The stirred solution was cooled to room temperature and seeded with crystals of the product 3 to facilitate crystallization. The precipitate was collected by vacuum filtration, washed with EtOH (100 mL) and dried in vacuo to give the pale brown solid (175 g), which was impure. The crude material was chromatographed over silica gel (hexane only) to give bisbenzylidene 3 (142.4 g, 83%) as a pale yellow solid. Physical data see A. B. Khasanov's Ph. D. Thesis (2000).

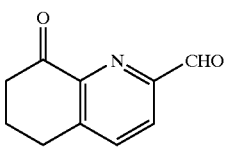

6,7-Dihydro-8(5H)-quinolinone-2-carboxaldehyde (4)

To a 1 L round-bottomed flask were added bisbenzylidene 3 (30.1 g, 93.1 mmol), $CH_2Cl_2$ (450 mL), and MeOH (150 mL). The solution was cooled to −78° C. and a stream Of $O_3/O_2$ was bubbled through the solution until it became blue. The resulting solution was purged by bubbling nitrogen gas for 20 mm, then $Me_2S$ (15 mL) was added at −78 C. The mixture was allowed to warm to room temperature overnight, and then the solvents were removed in vacuo. Ether (550 mL) was added the residue and the resulting solution was cooled in a freezer overnight. The pale yellow precipitate was collected by vacuum filtration, washed with ether and dried in vacuo to give ketoaldehyde 4 (11.8 g). Then ether was removed from the mother liquid in vacuo and the residue was dissolved in $CH_2Cl_2$ (300 mL). The solution was washed with water (40 mL×2), dried over $Na_2SO_4$, filtered and the solvent was evaporated in vacuo.

To the residue was added ether (300 mL) and the mixture was cooled in a freezer overnight. The pale yellow crystals were collected by vacuum filtration, washed with ether and dried in vacuo to give the same aldehyde 4 (3.22 g). Total yield of 5 is 15.0 g (92%). Physical data see A. B. Khasanov's Ph. D. Thesis (2000).

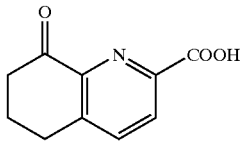

6,7-Dihydro-8(5H)-quinolinone-2-carboxylic acid (5)

To a 500 mL Erlenmeyer flask equipped with a stirring bar were added 6,7-dihydro-8(5H)-quinolinone-2-carboxaldehyde (4, 15.0 g, 85.6 mmol) and formic acid (17.0 g, 0.3 70 mmol). The mixture was stirred until clear solution was formed. Then 30% $H_2O_2$ aqueous solution (28.0 g) was added dropwise at 0° C. over a period of 10 mm. After the solid was formed, water (50 mL) was added and the resulting mixture was refrigerated overnight. The white precipitate was collected by vacuum filtration, washed with ice cold water and dried in vacuo to give carboxylic acid 5 (15.2 g, 93%). Physical data see A. B. Khasanov's Ph. D. Thesis (2000).

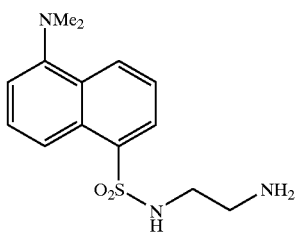

N1-(2-Aminoethyl)-5-(dimethylamino)-1-naphthalenesulfonalflide (6)

A 100 mL round-bottomed flask equipped with a stirring bar, 50 mL addition funnel and nitrogen gas inlet was charged with ethylenediamine (15 mL, 224 mmol) and $CH_2Cl_2$ (25 mL). The addition funnel was charged with a solution of dansyl chloride (1.00 g, 3.71 mmol) in $CH_2Cl_2$ (10 mL), which was added dropwise over a period of 30 mm to the vigorously stirred reaction mixture at room temperature under nitrogen atmosphere. After be stirring overnight, the resulting solution was diluted with $CH_2Cl_2$ (50 mL), washed with water (50 mL×3) and dried over $Na_2SO_4$. Evaporation of the solvent in vacuo followed by recrystallization from toluene/cyclohexane (3/2, 100 mL) afforded dansylamine derivative 6 (911 mg, 84%) as yellow-green needles. $^1H$ NMR (300 MHz, $CDCl_3$): δ8.53 (d, 1H, J=8.4 Hz, DnsH), 8.30 (d, 1H, J=9.0 Hz, DnsH), 8.25 (d, 1H, J=7.1 Hz, DnsH), 7.56 (t-like, 1H, J=8.2 Hz, DnsH, 7.52 (t-like, 1H, J=7.8 Hz, DnsH), 7.18 (d, 1H, J=7.8 Hz, DnsH), 2.89 (m. 11H, $NMe_2$, $SO_2NHCH_2$, $CH_2NH_2$), 2.69 (t, 2H, J=5.7 Hz, $CH_2NH_2$).

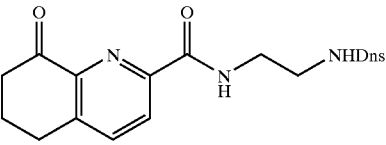

N-[(5-Dimethylamino)-1-naphthalenesulfonylamioethy]-6,7-dihydro-8(5H)-quinoline-2-carboxamide (7)

A 25 mL round-bottomed flask equipped with a stirring bar and a septum rubber was charged with keto-acid 5 (1.00 g, 5.23 mmol), $CH_2Cl_2$ (80 mL) and $Et_3N$ (2.9 mL, 20.8 mmol) at room temperature under nitrogen atmosphere. The mixture was cooled to −20° C. and then i-PrOCOCl (10 mL, 10 mmol, 1.0 M solution in PhMe) was added at the same temperature. The resulting solution was allowed to warm to ambient temperature overnight. Then amine 6 (1.84 g, 6.27 mmol) was added to the reaction mixture at room temperature and the stirring was continued overnight. After evaporation of the solvent in vacuo, the residue was chromatographed over alumina and silica gel successively to give keto-amide 7 (759 mg, 31%) as a yellow solid, which has $^1H$ NMR (300 MHz, $CDCl_3$): δ8.43 (d, 1H, J=8.4 Hz, DnsH), 8.36 (t, 1H, J=5.9 Hz, $SO_2NH$ $CH_2$), 8.25 (d, 1H, J=8.7 Hz, DnsH, 8.21 (d, 1H, J=7.5 Hz, DnsH), 8.10 (d, 1H, J=8.1 Hz, H3), 7.72 (d, 1H, J=8.1 Hz, H4), 7.45 (t, 1H, J=8.0 Hz, DnsH), 7.38 (t, 1H, J=8.1 Hz, DnsH), 7.03 (d, 1H, J=7.2 Hz, DnsH), 6.37 (t, 1H, J=5.5 Hz, $CONHCH_2$), 3.48 (q-like, 2H, J=5.9 Hz, $SO_2NHCH_2$), 3.16 (q-like, 2H, J=5.5 Hz, $CONHCH_2$), 3.03 (t, 2H, J=5.8 Hz, H7), 2.81 (s, 6H, $NMe_2$), 2.77 (m, 2H, H3), 2.17 (quint, J=6.1 Hz, H6); $^{13}C$ NMR (75 MHz, $CDCl_3$): δ196.2, 164.7, 151.7, 148.6, 146.3, 143.4, 139.0, 134.7, 130.2, 129.7, 129.50, 129.47, 128.1, 125.3, 123.1, 119.0, 114.9, 45.3 (×2), 43.4, 39.7, 39.4, 29.2, 22.3; Anal. Calcd. For $C_{24}H_{26}N_4O_4S$: C, 61.78; H, 5.62; N, 12.01%.

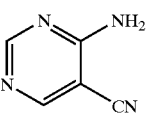

4-Amino-5-pyrimidinecarbonitrile (8)

A 1 L round-bottomed flask equipped with a stirring bar, 500 mL addition funnel and nitrogen gas inlet was charged with formamidine acetate (39.5 g, 379 mmol, freshly recrystallized from EtQH), malononitrile (12.8 g, 194 mmol, freshly recrystallized from t-butylmethylether) and anhydrous MeOH (210 mL). The addition funnel was charged with 2 M NaOMe solution in MeOH (210 mL), which was added dropwise over a period of 10 hr to the vigorously stirred reaction mixture. The resulting solution was stirred at room temperature for 2 days under nitrogen atmosphere and then cooled at 0° C. for 1.5 hr. The yellow precipitate was collected by vacuum filtration, washed with cold MeOH and dried in vacuo. The crude product 8 (20.9 g) was recrystallized from hot 10% AcOH aqueous solution (850 mL). The golden-yellow crystals formed at 0 C. were collected by vacuum filtration, washed with cold water (80 mL) and dried in vacuo to give aminonitrile 12 (13.3 g, 57%). Physical data see A. B. Khasanov's Ph. D. Thesis (2000).

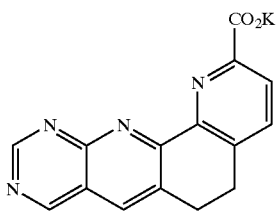

5,6-Dihydropyrimido[4,5-b][1,10]phenanthroline-2-carboxylic acid, potassium salt (9)

A 250 mL round-bottomed flask equipped with a stirring bar, condenser and nitrogen gas inlet was charged with 4-amino-5-pyrimidinecarboxaldehyde (8, 2.00 g, 16.2 mmol), carboxylic acid 5 (3. 10 g, 16.2 mmol) and MeOH (100 mL). The mixture was heated to boiling and then 1 N KOH solution in MeOH (19 mL) was added dropwise to achieve pH 9~10. The resulting mixture was heated under reflux, under nitrogen for 24 hr. Then the mixture was cooled to room temperature and refrigerated overnight. The precipitate was collected by vacuum filtration, washed with EtOH (30 mL) and dried in vacuo to give potassium salt 9 (4.17 g, 81%) as a gray solid. Physical data see A. B. Khasanov's Ph.D. Thesis (2000).

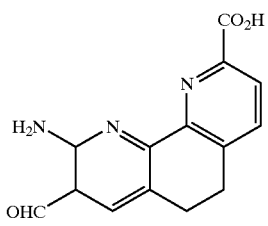

5,6-Dihydro-9-amino-8-[1,10] phenanthrolinecarboxaldehyde-2-carboxylic acid (10)

A 500 mL round-bottomed flask equipped with a stirring bar, condenser was charged with potassium salt 9 (4.17 g, 13.2 mmol) and water (200 mL). The solution was stirred and 15% HCl (3 mL) was added dropwise until the mixture reached pH 3–4 at room temperature. The suspension of precipitated yellow solid was heated under reflux for 15.5 hr. Then the mixture was cooled to room temperature, saturated with NaC 1 (60 g) and transferred into liquid-liquid continuous extractor attached to a 1 L round-bottomed flask, which contained EtOH/CHCl₃ (1/7, 500 mL). The suspension was extracted over a period of 4 days. Then the organic extract was dried over Na₂SO₄, filtered and the solvent was removed in vacuo to give aminoaldehyde 10 (3.05 g, 86%) as a yellow solid. Physical data see A. B. Khasanov's Ph. D. Thesis (2000).

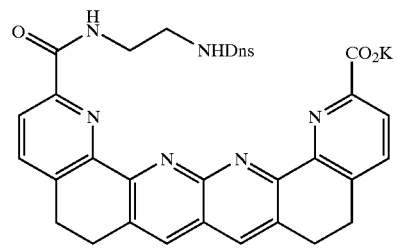

N-[(5-Dimethylamino)-1-naphthalenesulfonylaminoethyl]-5,6,9,10-tetrahydro[1,10]phenanthrolino[2,3-b][1,10] phenanthroline-13-carboxamide-2-carboxylic acid, potassium salt (11)

A 100 mL round-bottomed flask equipped with a stirring bar, condenser and nitrogen gas inlet was charged with aminoaldehyde 9 (173 mg, 0.643 mmol), keto-amide 7(300 mg, 0.643 mmol) and EtOH (40 mL). The mixture was heated to boiling and then 1 N KOH solution in MeOH (1.6 mL) was added dropwise over a period of 3 mm to achieve pH 9~10. The resulting mixture was refluxed for 5.5 days under nitrogen atmosphere. Then the solvent was removed in vacuo and ether (35 mL) and MeOH (10 mL) were added to the reside. The precipitate was collected by vacuum filtration, washed with ether and dried in vacuo to give potassium salt 11 (447 mg, 94%) as a light green solid.

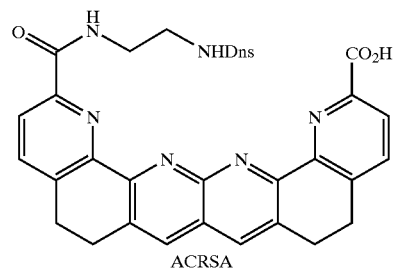

N-1(5-Dimethylamino)-1-naphthalenesulfonylaminoethyl]-5,6,9,10-tetrahydro [1,10]phenanthrolino[2,3-b][1,10] phenanthroline-13-carboxamide-2-carboxylic Acid (ACRSA)

To a 10 mL vial equipped with stirring bar were placed potassium salt 11 (447 mg, 0.60 mmol) and water (10 mL). The solution was stirred and 15% HCl (ca. 500 µL) was added dropwise until the mixture reached pH 3. After being refrigerated overnight, the orange precipitate was collected by vacuum filtration, washed with cold water and dried in vacuo to give Dns-acid ACRSA (322 mg, 76%) as an orange solid. Analytical sample was prepared by recrystallization from MeOH-CHCl₃ (8/5). ¹H NMR (300 MHz, CDCl₃): δ8.43 (d, 1H, J=8.4 Hz, DnsH), 8.36 (t, 1H, J=5.9 Hz, SO₂NHCH₂), 8.25 (d, 1H, J=8.7 Hz, DnsH), 8.21 (d, 1H, J=7.5 Hz, DnsH), 8.10 (d, 1H, J=8.1 Hz, H3), 7.72 (d, 1H, J=8.1 Hz, H4), 7.45 (t, 1H, J=8.0 Hz, DnsH), 7.38 (t, 1H, J=8.1 Hz, DnsH, 7.03 (d, 1H, J=7.2 Hz, DnsH), 6.37 (t, 1H, J=5.5 Hz, CONHCH₂), 3.48 (q-like, 2H, J=5.9 Hz, SO₂NHCH₂), 3.16 (q-like, 2H, J=5.5 Hz, CONHCH₂), 3.03 (t, 2H, J=5.8 Hz, H7), 2.81 (s, 6H, NMe₂), 2.77 (m, 2H, H3), 2.17 (quint, J=6.1 Hz, H6); ¹³C NMR (75 MHz, CDCl₃): δ165.5, 164.2, 154.5, 154.4, 154.1, 151.4, 149.6, 149.0, 148.5, 145.7, 139.3, 138.2, 137.4, 136.9, 135.2, 135.1, 134.9, 133.8, 133.7, 129.8, 129.5, 129.3, 128.9, 127.9, 124.3, 123.6, 122.8 (×2), 118.9, 114.7, 45.3 (×2), 43.4, 38.8, 27.5, 27.4, 27.2, 27.1; Anal. Calcd. For $C_{38}H_{33}N_7O_5S$: C, 65.22; H, 4.75; N, 14.01.

EXAMPLE 2
Detection of Arginine Compound

In this example, ACRSA (an arginine compound recognizing substance) detected the arginine compound by an increase in the intensity of ACRSA's fluorescence spectra.

The fluorescence spectra used in this Example were recorded on a Photon Technology International QM-1 Steady state Fluorescence system.

ACRSA was dissolved in a 95:5 mixture of methanol and methylene chloride. After the addition of $5.43 \times 10^{-5}$ M of arginine, the maximum fluorescence emission band at 412 of ACRSA increased to 125% of its original intensity.

EXAMPLE 3
Determining the Level of an Arginine Compound in a Body Fluid

This example discusses how an arginine recognizing substance can be used to detect arginine in a body sample.

An arginine recognizing substance is dissolved in chloroform (0.14 mM). Arginine obtained from commercial sources is dissolved in water at concentrations between about 0 $\mu$M to about 50 $\mu$M (0.1 mL, pH 6.0, 0.1 M MES buffer). The organic and aqueous solutions are shaken and the chromogenic response of the arginine recognizing substance is measured at each concentration.

A body sample of saliva is taken from a patient. The saliva is diluted with an equal volume of water. The pH of the solution is adjusted and 0.1 M MES buffer is added. 0.1 mL of the solution is added to the 0.14 mM solution of arginine recognizing substance in chloroform. The mixture is shaken and the chromogenic response of the arginine recognizing substance is measured and compared to the curve generated above.

Equivalents

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference.

What is claimed is:

1. A method for detecting arginine compounds in a body sample of a subject, comprising:
   contacting a body sample with an arginine compound recognizing substance which does not modify said arginine compound; and
   visually detecting the presence of said arginine compound by a change in color, wherein said arginine compound recognizing substance is of the formula:

$$G(N)_n(C)_m \quad (I)$$

wherein
   G is a guanidinium recognizing moiety;
   N is an ammonium recognizing moiety;
   C is a carboxylate recognizing moiety; and
   n and m are each independently integers from 0 to 10, and wherein said arginine compound recognizing substance coordinates to said arginine compound, such that arginine compounds are detected.

2. The method of claim 1, wherein said body sample is a body tissue.

3. The method of claim 2, wherein said body tissue is a tissue which utilizes the L-arginine nitric oxide pathway.

4. The method of claim 1, wherein said body sample is a body fluid.

5. The method of claim 4, wherein said body fluid is selected from the group consisting of urine, blood, saliva, sweat, and spinal and brain fluids.

6. The method of claim 5, further comprising obtaining said body fluid non-invasively.

7. The method of claim 1, wherein said arginine compound recognizing substance is an organic small molecule.

8. The method of claim 1, wherein said arginine compound is L-arginine.

9. The method of claim 1, wherein said arginine compound is $N^G$-monomethyl-L-arginine.

10. The method of claim 1, wherein said arginine compound is asymmetric dimethyl arginine.

11. The method of claim 1, wherein said arginine compound is symmetric dimethylarginine.

12. The method of claim 1, wherein n and m are 1.

13. The method of claim 1, wherein G is multicyclic.

14. The method of claim 13, wherein G comprises at least one heterocycle.

15. The method of claim 1, wherein G is hydrogen-bond forming.

16. The method of claim 1, wherein G is anionic.

17. The method of claim 1, wherein G is a guanidinium recognizing moiety for non-methylated guanidine, monomethylated guanidine, symmetric dimethylated guanidine or asymmetric dimethylated guanidine.

18. The method of claim 17, wherein said guanidinium recognizing moiety is a guanidinium recognizing moiety for asymmetric dimethylated guanidine.

19. The method of claim 18, wherein said guanidinium recognizing moiety for asymmetric dimethylated guanidine is selected from the group consisting of:

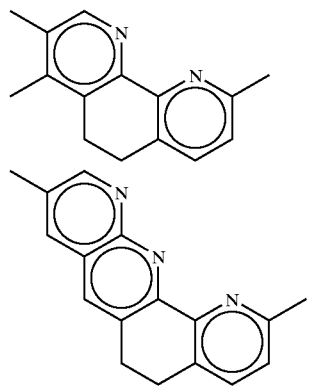

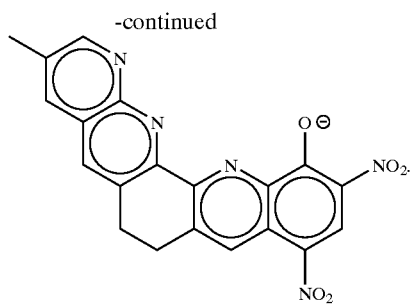

20. The method of claim 1, wherein said guanidinium recognizing moiety is selected from the group consisting of:

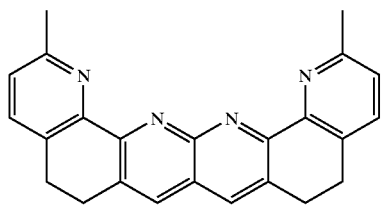

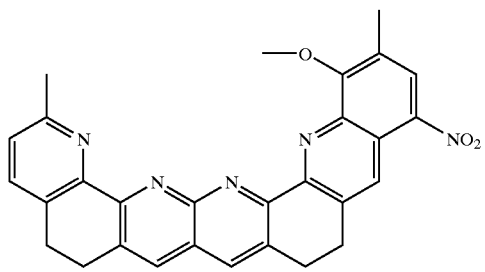

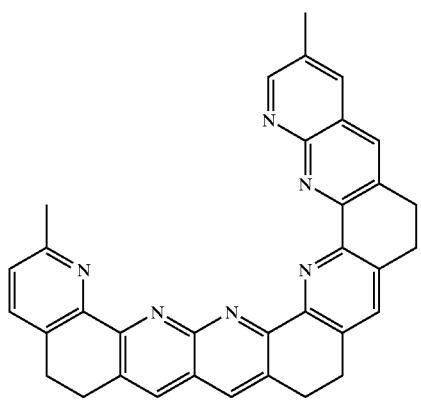

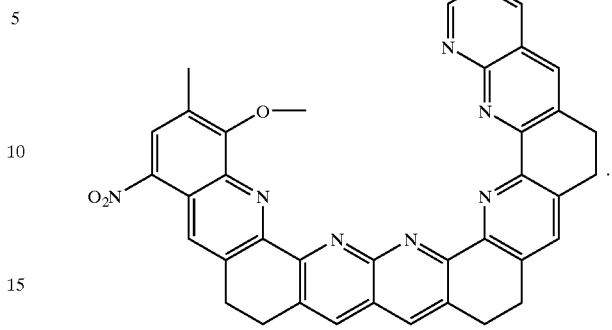

21. The method of claim 1, wherein said ammonium recognizing moiety is neutral or anionic.

22. The method of claim 1, wherein said ammonium recognizing moiety comprises one or more heteroatoms.

23. The method claim 22, wherein said ammonium recognizing moiety comprises a moiety selected from the group consisting of carbonyl, amide, hydroxyl, hydroxime, carboxylate, ether, ester, pyridine, pyrimidine, phenolate, phosphate, and combinations thereof.

24. The method of claim 22, wherein said ammonium recognizing moiety is selected from the group consisting of:

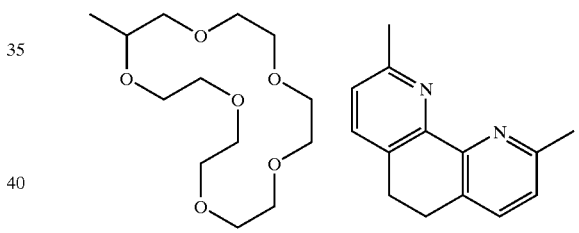

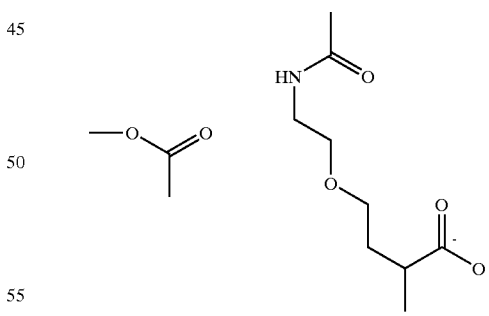

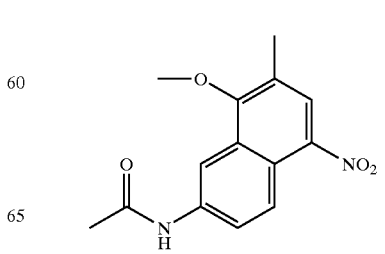

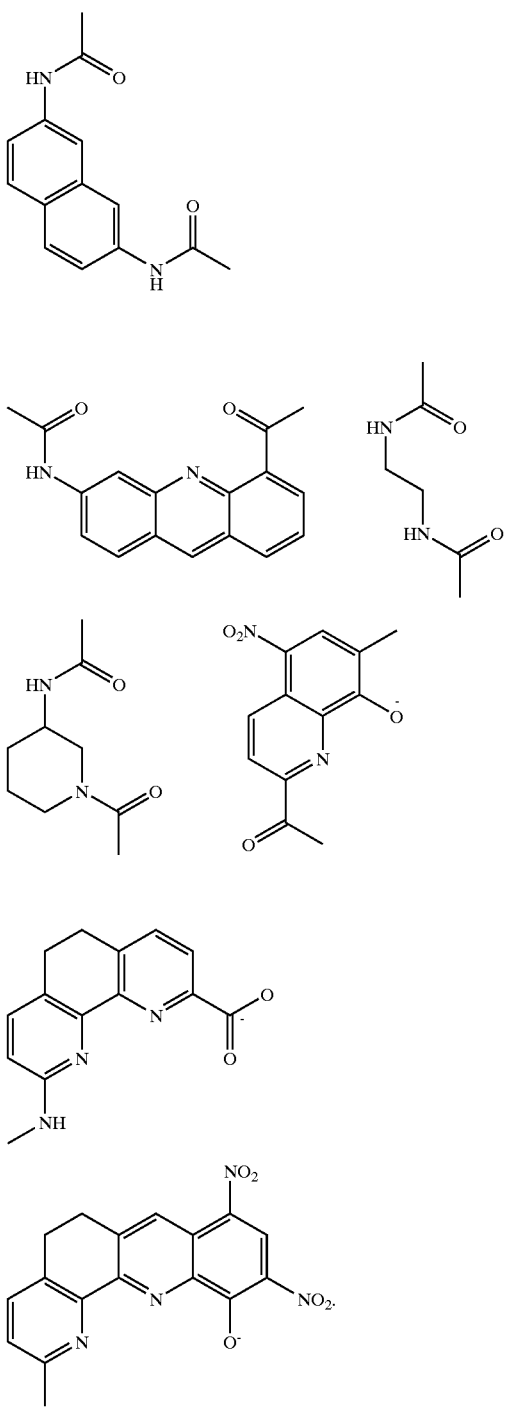

wherein Z is alkyl, alkenyl, alkynyl, hydrogen, acyl, hydrogen, or a halogen atom.

28. The method of claim 1, wherein said arginine compound recognizing substance further comprises at least one linking moiety.

29. The method of claim 1, wherein said arginine compound recognizing substance is an arginine recognizing substance.

30. The method of claim 1, wherein said arginine compound recognizing substance is an asymmetric dimethyl arginine recognizing substance.

31. The method of claim 30, wherein said asymmetric dimethyl arginine recognizing substance is of the formula:

$$Q(N)_n(C)_m \qquad (II)$$

25. The method of claim 1, wherein said carboxylate recognizing moiety is neutral or cationic.

26. The method of claim 25, wherein said cationic carboxylate recognizing moiety is a guanidinium or ammonium ion, optionally linked to additional hydrogen-bond donating groups.

27. The method of claim 25, wherein said carboxylate recognizing moieties is selected from the group consisting of:

wherein

Q is a dimethylated guanidinium recognizing moiety for asymmetric dimethylated guanidine;

N is an ammonium recognizing moiety;

C is a carboxylate recognizing moiety, and n and m are each independently integers from 0 to 10.

32. The method of claim 31, wherein n and m are each 1.

33. The method of claim 1, wherein said arginine compound recognizing substance is:

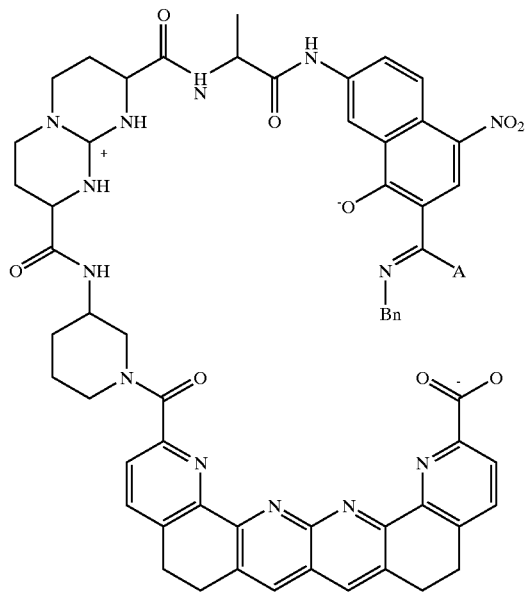

wherein X is hydrogen, alkyl, alkenyl, alkynyl, aryl, halogen, chromophore, or a fluorophore.

34. A method for determining arginine compound levels in a body sample of a subject, comprising:

contacting a body sample with a arginine recognizing substance; and analyzing the resulting mixture optically, such that arginine compound levels are determined, wherein said arginine recognizing substance is selected from the group consisting of:

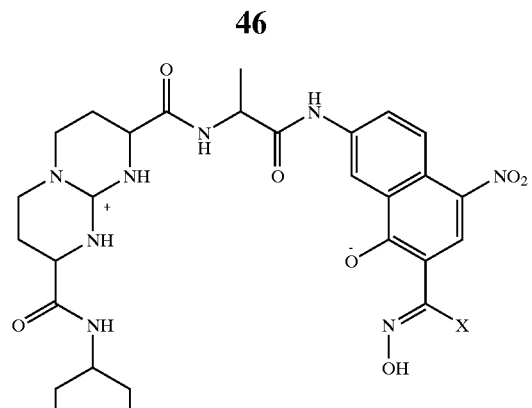

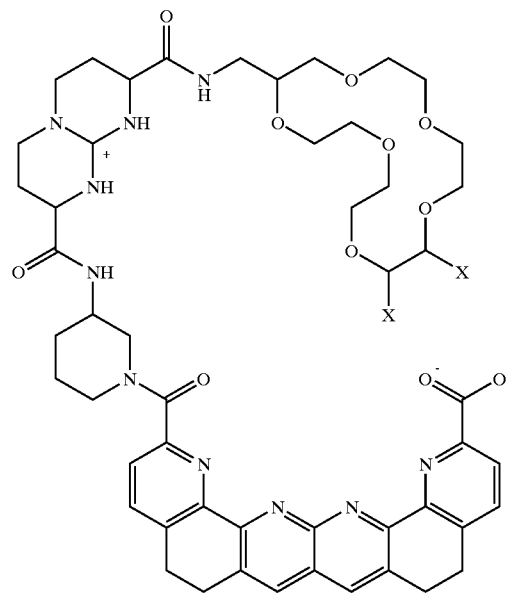

47
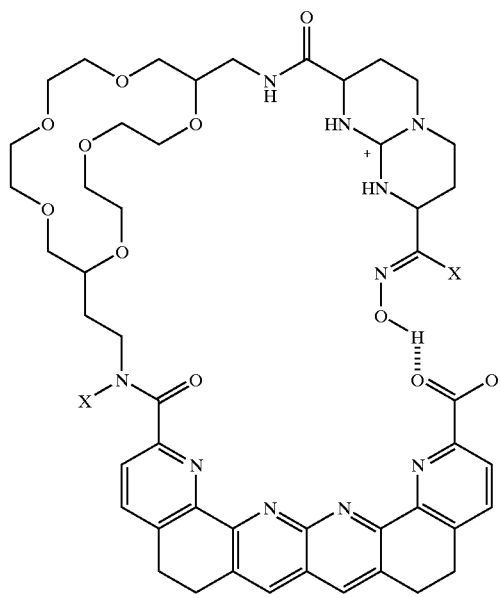
48
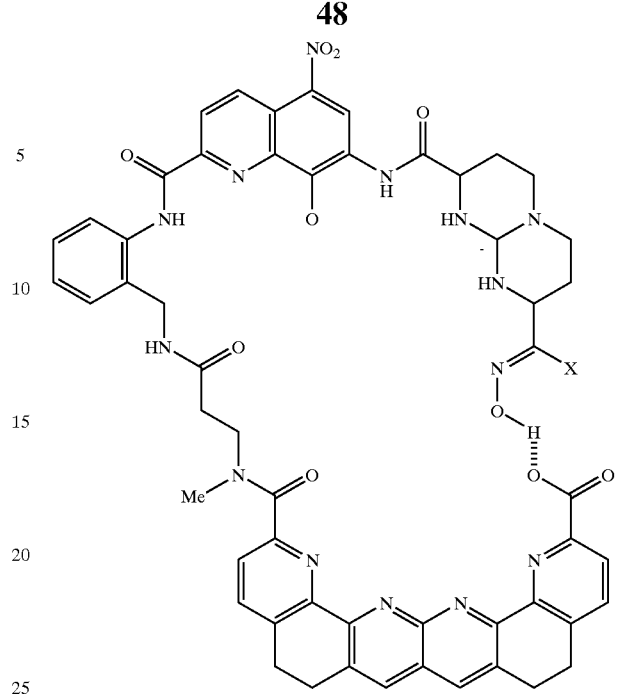
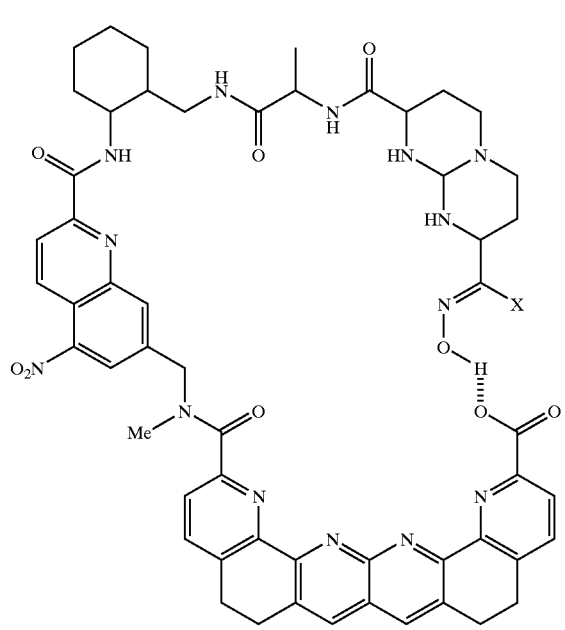
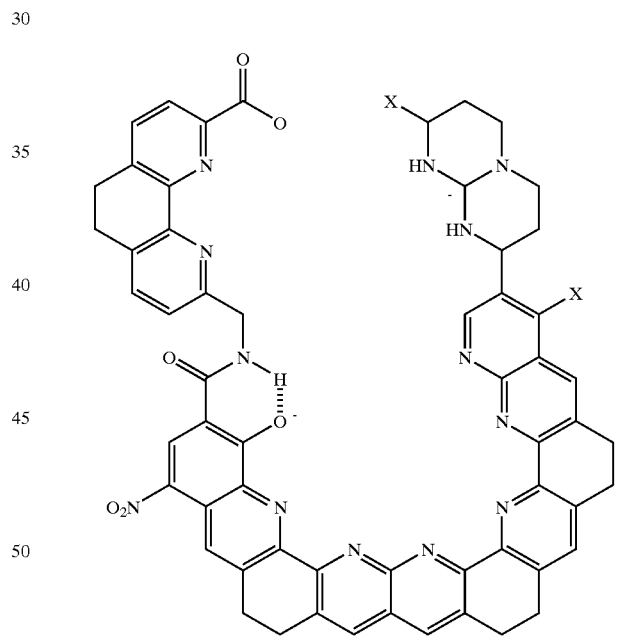

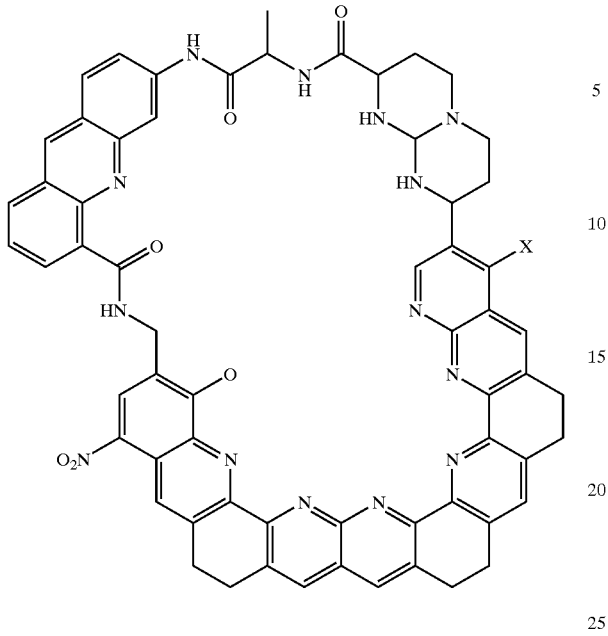

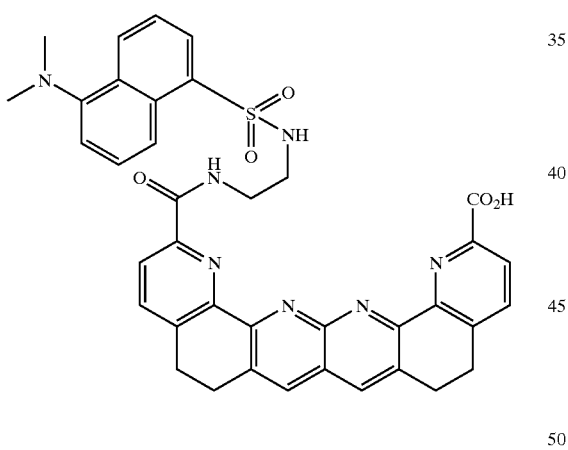

wherein X is hydrogen, alkyl, alkenyl, alkynyl, aryl, halogen, chromophore, or a fluorophore.

35. A method for determining asymmetric dimethyl arginine levels in a body sample of a subject, comprising:

contacting a body sample with a asymmetric dimethyl arginine recognizing substance; and analyzing the resulting mixture optically, such that asymmetric dimethyl arginine compound levels are determined, wherein said asymmetric dimethyl arginine recognizing substance is selected from the group consisting of:

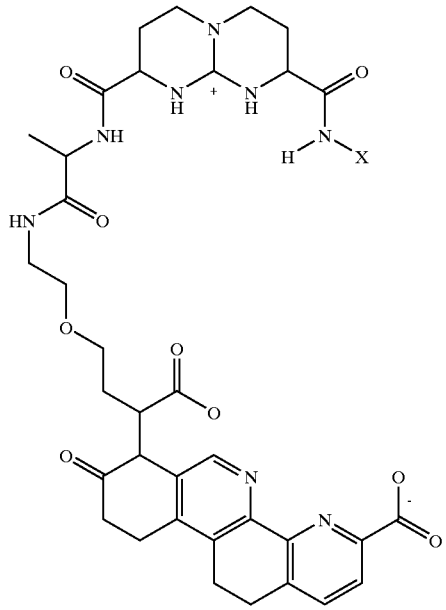

51
-continued
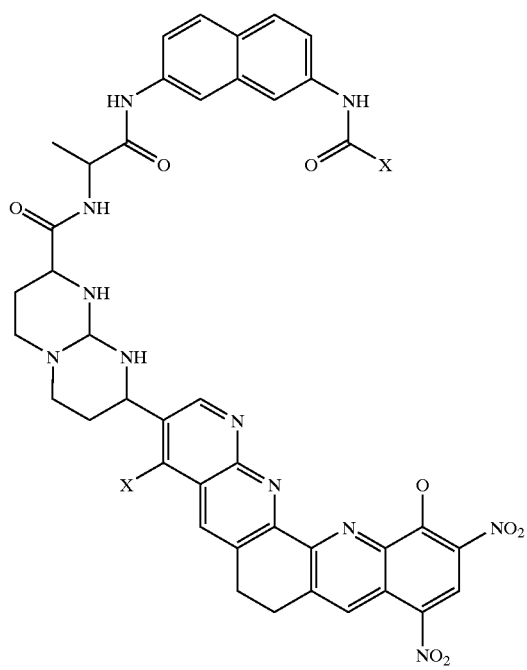
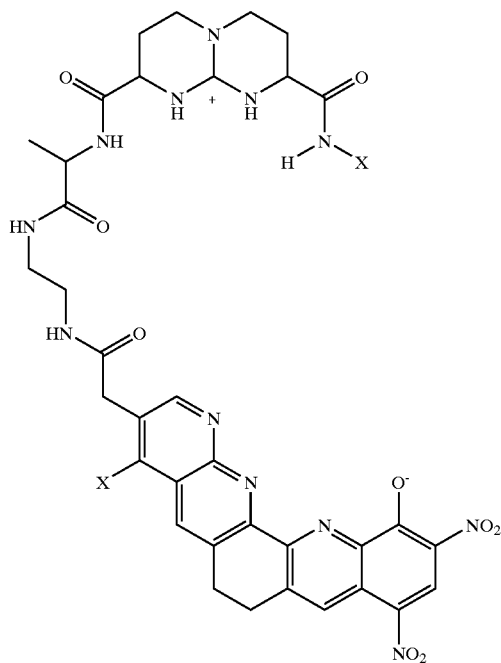
52
-continued
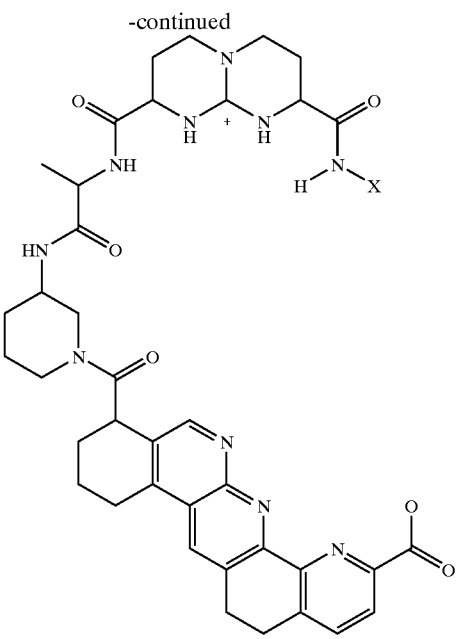
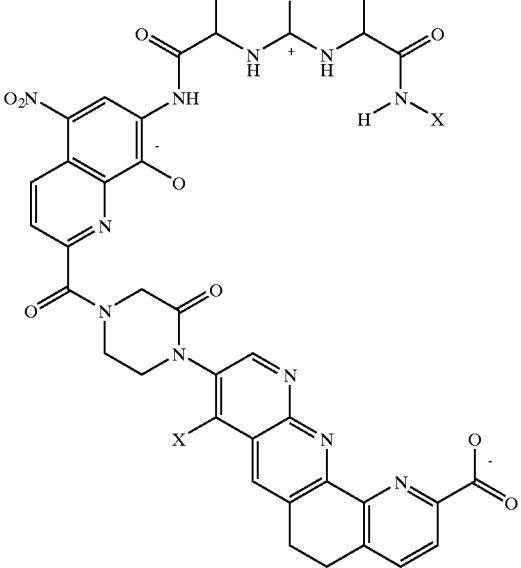

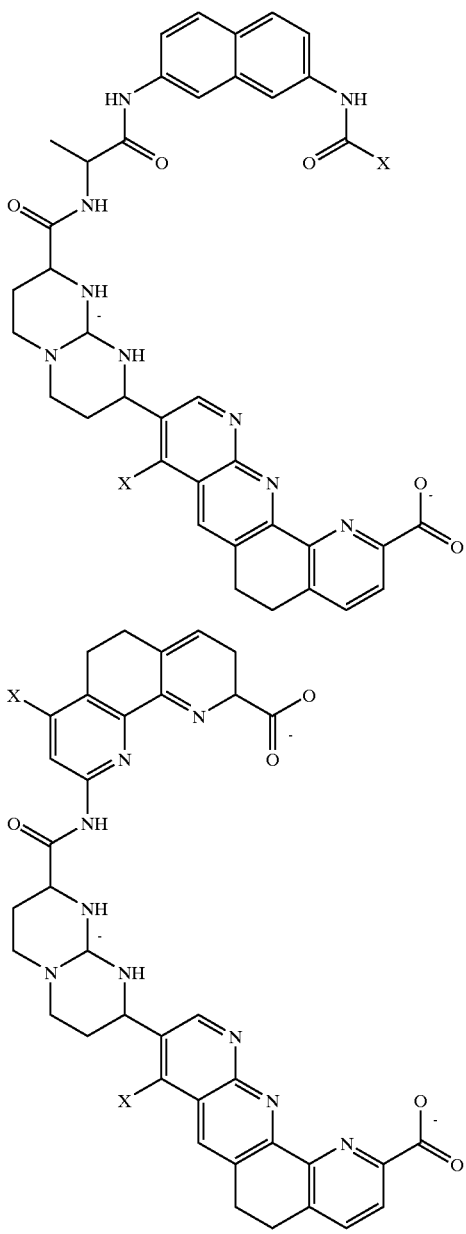
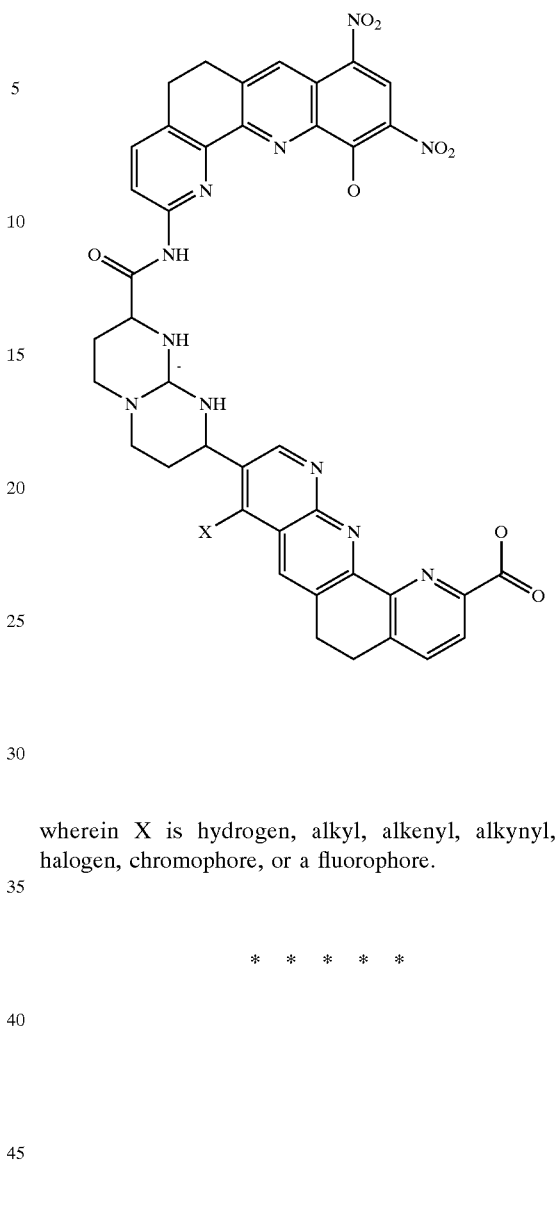
wherein X is hydrogen, alkyl, alkenyl, alkynyl, aryl, halogen, chromophore, or a fluorophore.
* * * * *